United States Patent
Rheinheimer et al.

(10) Patent No.: US 6,586,369 B1
(45) Date of Patent: Jul. 1, 2003

(54) FUNGICIDAL AGENTS CONTAINING PYRROLIDONES AS THEIR ACTIVE AGENTS AND USE THEREOF FOR TREATING PLANTS

(75) Inventors: Joachim Rheinheimer, Ludwigshafen (DE); Karl Eicken, Wachenheim (DE); Ingo Rose, Mannheim (DE); Thomas Grote, Wachenheim (DE); Eberhard Ammermann, Heppenheim (DE); John-Bryan Speakman, Bobenheim (DE); Siegfried Strathmann, Limburgerhof (DE); Gisela Lorenz, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/204,349
(22) PCT Filed: Feb. 23, 2001
(86) PCT No.: PCT/EP01/02059
§ 371 (c)(1),
(2), (4) Date: Aug. 20, 2002
(87) PCT Pub. No.: WO01/62087
PCT Pub. Date: Aug. 30, 2001

(30) Foreign Application Priority Data

Feb. 26, 2000 (DE) .......................... 100 09 115

(51) Int. Cl.$^7$ .................. C07D 207/18; A01N 43/36
(52) U.S. Cl. ................ 504/283; 548/546; 548/235; 548/247; 504/225; 504/248; 504/270; 504/271; 544/141; 546/208
(58) Field of Search ................ 504/225, 248, 504/270, 271, 283; 548/235, 247, 546; 544/141; 546/208

(56) References Cited

FOREIGN PATENT DOCUMENTS

| JP | 50-117929 | 9/1975 |
|----|-----------|--------|
| WO | 00 30445 | 6/2000 |

OTHER PUBLICATIONS

Database Chemabs, XP 002176192.
XP–000901338.
JP 0117–929.

Primary Examiner—Ceila Chang
Assistant Examiner—Golam M. M. Shameem
(74) Attorney, Agent, or Firm—Keil & Weinkauf

(57) ABSTRACT

Agrochemical compositions having fungicidal action and comprising as active compounds compounds of the formula I

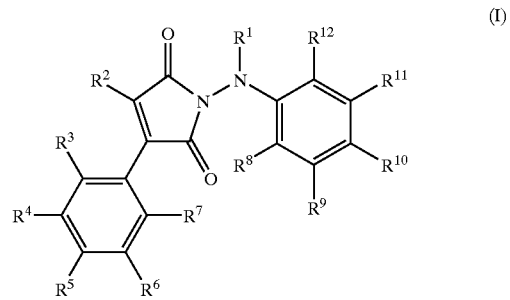

where $R^1$ is hydrogen, $C_1$–$C_6$-alkyl, $C_1$–$C_6$-alkylcarbonyl, formyl or $C_1$–$C_6$-haloalkylcarbonyl;

$R^2$ is halogen, $C_1$–$C_6$-alkylthio, $C_1$–$C_6$-alkoxy, $C_3$–$C_6$-cycloalkyl-$C_1$–$C_6$-alkoxy, $C_1$–$C_6$-alkoxy-$C_1$–$C_6$-alkyl, halo-$C_1$–$C_6$-alkoxy, $C_1$–$C_6$-alkylsulfonyl, $C_1$–$C_6$-alkylsulfinyl, halo-$C_1$–$C_6$-alkylsulfonyl, cyano or a radical $NR^{13}R^{14}$;

$R^3$–$R^{12}$ are hydrogen, halogen, $C_1$–$C_8$-cycloalkyl, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkylsulfonyl, halo-$C_1$–$C_6$-alkylsulfonyl, formyl, $C_1$–$C_6$-alkylcarbonyl, cyano, $C_1$–$C_6$-alkylthio or phenyl, which may be unsubstituted or substituted by halogen, $C_1$–$C_6$-alkyl or halo-$C_1$–$C_6$-alkyl, $R^{13}$ is hydrogen, $C_1$–$C_6$-alkyl, $R^{14}$ is $C_1$–$C_6$-alkyl, $C_1$–$C_8$-cycloalkyl or, together with $R^{13}$ and the nitrogen atom to which they are attached, a saturated or unsaturated heterocyclic five- or six-membered ring which contains one or two heteroatoms selected from the group consisting of nitrogen and oxygen, and their agriculturally useful salts are described.

16 Claims, No Drawings

FUNGICIDAL AGENTS CONTAINING PYRROLIDONES AS THEIR ACTIVE AGENTS AND USE THEREOF FOR TREATING PLANTS

This application is a 371 of PCT/EP01/02059 Feb. 23, 2001.

The present invention relates to novel agrochemical compositions having fungicidal action and comprising pyrrolidones as active compounds, and to their use in the treatment of plants and in agriculture.

The present invention provides compositions comprising as active compounds compounds of the formula I

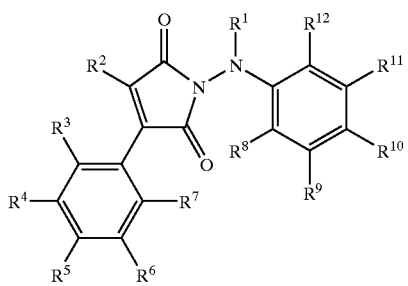

where:
- $R^1$ is hydrogen, $C_1$–$C_6$-alkyl, $C_1$–$C_6$-alkylcarbonyl, formyl or $C_1$–$C_6$-haloalkylcarbonyl;
- $R^2$ is halogen, $C_1$–$C_6$-alkylthio, $C_1$–$C_6$-alkoxy, $C_3$–$C_6$-cycloalkyl-$C_1$–$C_6$-alkoxy, $C_1$–$C_6$-alkoxy-$C_1$–$C_6$-alkyl, halo-$C_1$–$C_6$-alkoxy, $C_1$–$C_6$-alkylsulfonyl, $C_1$–$C_6$-alkylsulfinyl, halo-$C_1$–$C_6$-alkylsulfonyl, cyano or a radical $NR^{13}R^{14}$;
- $R^3$–$R^{12}$ are hydrogen, halogen, $C_1$–$C_8$-cycloalkyl, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkylsulfonyl, halo-$C_1$–$C_6$-alkylsulfonyl, formyl, $C_1$–$C_6$-alkylcarbonyl, cyano, $C_1$–$C_6$-alkylthio or phenyl, which may be unsubstituted or substituted by halogen, $C_1$–$C_6$-alkyl or halo-$C_1$–$C_6$-alkyl,
- $R^{13}$ is hydrogen, $C_1$–$C_6$-alkyl,
- $R^{14}$ is $C_1$–$C_6$-alkyl, $C_1$–$C_8$-cycloalkyl or, together with $R^{13}$ and the nitrogen atom to which they are attached, a saturated or unsaturated heterocyclic five- or six-membered ring which contains one or two heteroatoms selected from the group consisting of nitrogen and oxygen, and their agriculturally useful salts.

Some of the compounds of the formula I are known from the literature. Thus, for example, Z. Chem. 13, (1973), 214–216 (M. Augustin and P. Reinemann) describes phenyl substituted pyrrolidones. A fungicidal action of these compounds has hitherto not been described.

Surprisingly, it has been found that compounds of the formula I have a remarkable fungicidal action. They are suitable for controlling harmful fungi in the treatment of plants, and also for the therapeutic treatment of human disorders caused by harmful fungi, and for the veterinary treatment of mammals.

Compounds of the formula I can be prepared similarly to the process described in the literature (Z. Chem. 13, (1973), 214–216). The starting materials are either known from the literature or commercially available.

In the definition of the substituents $R^1$ to $R^{12}$, the given terms are collective terms for a group of compounds. The alkyl radicals mentioned in each case each denote straight-chain or branched alkyl radicals having up to six carbon atoms.

Halogen is in each case fluorine, bromine, chlorine or iodine, in particular fluorine or chlorine.

Examples of Other Meanings are:
- $C_1$–$C_6$-alkyl: a straight-chain or branched alkyl group, such as, for example, methyl, ethyl, n-propyl, 1-methylethyl, n-butyl, 1-methylpropyl, 2-methylpropyl or 1,1-dimethylethyl, in particular ethyl;
- $C_1$–$C_6$-haloalkyl: a $C_1$–$C_6$-alkyl radical as mentioned above which is partially or fully substituted, in particular mono-, di- or trisubstituted, by fluorine, chlorine, bromine and/or iodine, for example trichloromethyl, trifluoromethyl, 2-fluoroethyl, 2-chloroethyl, 2-bromoethyl, 2,2-difluoroethyl, 2,2,2-trifluoroethyl, 2,2,2-trichloroethyl, 2-fluoropropyl, 3-fluoropropyl, 2-chloropropyl or 3-chloropropyl, in particular 2-fluoroethyl or 2-chloroethyl;
- $C_1$–$C_6$-alkoxy: a straight-chain or branched alkoxy radical having up to six carbon atoms, such as, for example, methoxy, ethoxy, n-propoxy, 1-methylethoxy, n-butoxy, 1-methylpropoxy, 2-methylpropoxy or 1,1-dimethylethoxy, in particular methoxy or ethoxy;
- $C_1$–$C_6$-alkoxy-$C_1$–$C_6$-alkyl: an alkyl radical as mentioned above which is substituted by $C_1$–$C_6$-alkoxy, as mentioned above, such as, for example, methoxymethyl, ethoxymethyl, n-propoxymethyl, 1-methylethoxymethyl or n-butoxymethyl;
- $C_3$–$C_8$-cycloalkyl: a saturated cycloalkyl group, such as, for example, cyclopropyl, cyclobutyl, cyclopentyl, cyclohexyl, cycloheptyl, cyclooctyl;
- $C_3$–$C_8$-cycloalkyl-$C_1$–$C_6$-alkoxy: an alkoxy group as mentioned above which is substituted by $C_3$–$C_8$-cycloalkyl as mentioned above, such as, for example, cyclopropylmethoxy, cyclobutylmethoxy, cyclopentylmethoxy, cyclohexylmethoxy, cycloheptylmethoxy, cyclooctylmethoxy, cyclopropylethoxy, cyclobutylethoxy, cyclopentylethoxy, cyclohexylethoxy, cycloheptylethoxy, cyclooctylethoxy;
- halo-$C_1$–$C_6$-alkoxy: a $C_1$–$C_6$-alkoxy radical as mentioned above which is mono-, di- or trisubstituted by fluorine, chlorine or bromine, such as, for example, chloromethoxy, fluoromethoxy, difluoromethoxy, difluoroethoxy, dichloromethoxy, dichloroethoxy;
- $C_1$–$C_6$-alkyl-carbonyl: a carbonyl group which is substituted by a $C_1$–$C_6$-alkyl radical as above, such as, for example, acetyl, propionyl, butyryl;
- halogen-$C_1$–$C_6$-alkyl-carbonyl: a $C_1$–$C_6$-alkyl-carbonyl radical as above which is substituted by fluorine, chlorine or bromine;
- $C_1$–$C_6$-alkylsulfonyl: a sulfonyl group which is substituted by a $C_1$–$C_6$-alkyl radical as mentioned above,
- $C_1$–$C_6$-alkylsulfinyl: a sulfinyl group which is substituted by a $C_1$–$C_6$-alkyl radical as mentioned above;
- halo-$C_1$–$C_6$-alkylsulfonyl: a $C_1$–$C_6$-alkylsulfonyl radical as mentioned above which is substituted by fluorine, chlorine or bromine;
- $C_1$–$C_6$-alkylthio: a sulfur atom which is substituted by a $C_1$–$C_6$-alkyl radical as mentioned above;
- an unsubstituted or substituted phenyl radical: a phenyl radical which is unsubstituted or mono- or polysubstituted. Any substituents are possible, for example the following: halogen atoms, $C_1$–$C_6$-alkyl or halo-$C_1$–$C_6$-alkyl. The phenyl radical is preferably mono-, di- or trisubstituted.

If $R^{13}$ and $R^{14}$ together with the nitrogen to which they are attached form a chain of 4–5 carbon atoms, they are saturated or partially unsaturated heterocyclic 5- or 6-membered rings containing one or two heteroatoms (oxygen or nitrogen atoms), such as, for example, pyrrole, oxazole, isoxazole, morpholino or piperidino.

For the purpose of the present invention, preferably with respect to the definitions of substituents mentioned, the following compounds are possible, in each case on their own or in combination with one another:

1. Compounds of the formula I in which $R^1$ has the following meanings: hydrogen; $C_1$–$C_3$-alkyl (such as, for example, methyl, ethyl); $C_1$–$C_3$-alkylcarbonyl (for example acetyl); formyl; in particular hydrogen, formyl, acetyl or methyl.
2. Compounds according to item 1, where $R^2$ has the following meanings: chlorine, bromine, $C_1$–$C_3$-alkylthio (for example methylthio); $C_1$–$C_6$-alkylsulfonyl (for example methylsulfonyl); $C_1$–$C_6$-alkylsulfinyl (for example methylsulfinyl); $C_1$–$C_3$-haloalkoxy (for example difluoromethoxy); in particular chlorine and bromine.
3. Compounds according to items 1 or 2, where $R^3$–$R^{12}$ have the following meanings: hydrogen; fluorine; chlorine; $C_1$–$C_4$-alkyl (for example methyl, ethyl, propyl, butyl); halo-$C_1$–$C_3$-alkyl (for example trifluoromethyl, difluoromethyl); halo-$C_1$–$C_3$-alkoxy (for example trifluoromethoxy, difluoromethoxy); $C_1$–$C_3$-alkoxy (for example methoxy); $C_1$–$C_3$-alkylthio (for example methylthio); cyano.
4. Compounds according to items 1 to 3 where at least two of the radicals $R^8$–$R^{12}$ and furthermore at least two of the radicals $R^3$–$R^7$ are hydrogen and the others are hydrogen, fluorine, chlorine; $C_1$–$C_4$-alkyl (for example methyl, ethyl, propyl, butyl); halo-$C_1$–$C_3$-alkyl (for example trifluoromethyl); halo-$C_1$–$C_3$-alkoxy (for example trifluoromethoxy, difluoromethoxy).

The two phenyl rings are preferably unsubstituted ($R^3$–$R^{12}$=H) or preferably mono-, di- or trisubstituted, where preference is given to the following substituents: $C_1$–$C_6$-alkyl, halogen, halo-$C_1$–$C_6$-alkyl, halo-$C_1$–$C_6$-alkoxy. In this context, particular preference is given to the following substituents: methyl, isopropyl, fluorine, chlorine, trifluoromethyl or trifluoromethoxy.

The compounds mentioned above have usually been found to be particularly effective.

For the purpose of the present invention, suitable fungicidally active compounds are, for example, the following compounds in Table 1.

TABLE 1

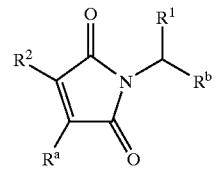

II

| No. | $R^1$ | $R^2$ | $R^a$ | $R^b$ | Phys. Data |
|---|---|---|---|---|---|
| 1) | H | Cl | phenyl | phenyl | m.p. 143–145° C. |
| 2) | H | Cl | phenyl | 4-methylphenyl | |
| 3) | H | Cl | phenyl | 2,4-dichlorophenyl | |
| 4) | H | Cl | 4-methylphenyl | phenyl | |
| 5) | H | Cl | 4-methylphenyl | 4-chlorophenyl | |
| 6) | H | Cl | 4-methoxyphenyl | phenyl | m.p. 148–149° C. |
| 7) | H | Cl | 4-methoxyphenyl | 4-methoxyphenyl | |
| 8) | H | Cl | 4-methoxyphenyl | 2-methoxyphenyl | |
| 9) | H | Cl | 4-methoxyphenyl | 4-chlorophenyl | |
| 10) | H | Cl | 4-methoxyphenyl | 2,4-dichlorophenyl | |
| 11) | H | Cl | 3-chlorophenyl | phenyl | m.p. 130–132° C. |
| 12) | H | Cl | 3,4-dichlorophenyl | phenyl | |
| 13) | H | Cl | 4-chlorophenyl | phenyl | |
| 14) | H | Cl | 4-chlorophenyl | 4-chlorophenyl | |
| 15) | H | Cl | 4-chlorophenyl | 3,4-dichlorophenyl | |
| 16) | H | Cl | 4-chlorophenyl | 2,4-dichlorophenyl | |
| 17) | H | Cl | 4-chlorophenyl | 4-fluorophenyl | |
| 18) | H | Cl | 4-chlorophenyl | 4-methylphenyl | |
| 19) | H | Cl | 4-bromophenyl | 4-methoxyphenyl | |
| 20) | H | Cl | 4-bromophenyl | 4-methylphenyl | |
| 21) | methyl | Cl | 4-methylphenyl | phenyl | |
| 22) | methyl | Cl | 4-methoxyphenyl | phenyl | |
| 23) | methyl | Cl | 4-chlorophenyl | phenyl | m.p. 165–166° C. |
| 24) | acetyl | Cl | phenyl | phenyl | |
| 25) | trifluoro-acetyl | Cl | phenyl | phenyl | |
| 26) | H | Cl | phenyl | 4-isopropylphenyl | |
| 27) | H | Cl | phenyl | 4-fluorophenyl | m.p. 127–128° C. |
| 28) | H | Cl | phenyl | 3-fluorophenyl | |
| 29) | H | Cl | phenyl | 2-fluorophenyl | |
| 30) | H | Cl | phenyl | 2,3,5,6-tetra-fluorophenyl | |
| 31) | H | Cl | phenyl | 4-trifluoromethylphenyl | |
| 32) | H | Cl | phenyl | 3-trifluoromethylphenyl | |

TABLE 1-continued

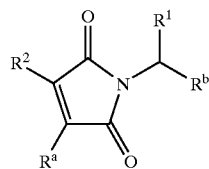

| No. | R¹ | R² | Rᵃ | Rᵇ | Phys. Data |
|---|---|---|---|---|---|
| 33) | H | Cl | phenyl | 4-methylsulfonylphenyl | |
| 34) | H | Cl | phenyl | 4-chlorophenyl | |
| 35) | H | Cl | phenyl | 3-chlorophenyl | |
| 36) | H | Cl | phenyl | 2-chlorophenyl | |
| 37) | H | Cl | phenyl | 3,5-dichlorophenyl | |
| 38) | H | Cl | phenyl | 4-(trifluoromethoxy)phenyl | |
| 39) | H | Cl | phenyl | 3-(trifluoromethoxy)phenyl | |
| 40) | H | Cl | phenyl | 4-(difluoromethoxy)phenyl | |
| 41) | H | Cl | phenyl | 3-(difluoromethoxy)phenyl | |
| 42) | H | Cl | phenyl | 4-cyanophenyl | |
| 43) | H | Cl | 4-chlorophenyl | 4-trifluoromethylphenyl | |
| 44) | H | Cl | 4-chlorophenyl | 3-trifluoromethylphenyl | |
| 45) | H | Cl | 4-chlorophenyl | 2-chlorophenyl | |
| 46) | H | Cl | 4-chlorophenyl | 3-chlorophenyl | |
| 47) | H | Cl | 4-chlorophenyl | 4-trifluoromethoxyphenyl | |
| 48) | H | Cl | 4-chlorophenyl | 3-trifluoromethoxyphenyl | |
| 49) | H | Cl | 4-chlorophenyl | 4-difluoromethoxyphenyl | |
| 50) | H | Cl | 4-chlorophenyl | 3-difluoromethoxyphenyl | |
| 51) | H | Cl | 4-fluorophenyl | phenyl | |
| 52) | H | Cl | 4-fluorophenyl | 4-ethylphenyl | |
| 53) | H | Cl | 4-fluorophenyl | 4-methylphenyl | |
| 54) | H | Cl | 4-fluorophenyl | 2-methylphenyl | |
| 55) | H | Cl | 4-fluorophenyl | 3-methylphenyl | |
| 56) | H | Cl | 4-fluorophenyl | 4-fluorophenyl | |
| 57) | H | Cl | 4-fluorophenyl | 2,4-difluorophenyl | |
| 58) | H | Cl | 4-fluorophenyl | 4-chlorophenyl | |
| 59) | H | Cl | 4-fluorophenyl | 3-chlorophenyl | |
| 60) | H | Cl | 4-fluorophenyl | 2-chlorophenyl | |
| 61) | H | Cl | 4-fluorophenyl | 4-chloro-2-methoxyphenyl | |
| 62) | H | Cl | 4-fluorophenyl | 4-trifluoromethylphenyl | |
| 63) | H | Cl | 4-fluorophenyl | 2-trifluoromethylphenyl | |
| 64) | H | Cl | 4-fluorophenyl | 3-trifluoromethylphenyl | |
| 65) | H | Cl | 4-fluorophenyl | 4-(trifluormethoxy)phenyl | |
| 66) | H | Cl | 4-fluorophenyl | 3-(trifluoromethoxy)phenyl | |
| 67) | H | Cl | 4-fluorophenyl | 4-(difluoromethoxy)phenyl | |
| 68) | H | Cl | 4-fluorophenyl | 3-(difluoromethoxy)phenyl | |
| 69) | H | Cl | 4-fluorophenyl | 4-cyanophenyl | |
| 70) | H | Cl | 3-fluorophenyl | phenyl | |
| 71) | H | Cl | 3-fluorophenyl | 4-ethylphenyl | |
| 72) | H | Cl | 3-fluorophenyl | 4-methylphenyl | |
| 73) | H | Cl | 3-fluorophenyl | 2-methylphenyl | |
| 74) | H | Cl | 3-fluorophenyl | 3-methylphenyl | |
| 75) | H | Cl | 3-fluorophenyl | 4-fluorophenyl | |
| 76) | H | Cl | 3-fluorophenyl | 2,4-difluorophenyl | |
| 77) | H | Cl | 3-fluorophenyl | 4-chlorophenyl | |
| 78) | H | Cl | 3-fluorophenyl | 3-chlorophenyl | |
| 79) | H | Cl | 3-fluorophenyl | 2-chlorophenyl | |
| 80) | H | Cl | 3-fluorophenyl | 4-chloro-2-methoxyphenyl | |
| 81) | H | Cl | 3-fluorophenyl | 4-trifluoromethylphenyl | |
| 82) | H | Cl | 3-fluorophenyl | 2-trifluoromethylphenyl | |
| 83) | H | Cl | 3-fluorophenyl | 3-trifluoromethylphenyl | |
| 84) | H | Cl | 3-fluorophenyl | 4-(trifluoromethoxy)phenyl | |
| 85) | H | Cl | 3-fluorophenyl | 3-(trifluoromethoxy)phenyl | |
| 86) | H | Cl | 3-fluorophenyl | 4-(difluoromethoxy)phenyl | |
| 87) | H | Cl | 3-fluorophenyl | 3-(difluoromethoxy)phenyl | |
| 88) | H | Cl | 3-fluorophenyl | 4-cyanophenyl | |
| 89) | H | Cl | 2-fluorophenyl | phenyl | |
| 90) | H | Cl | 2-fluorophenyl | 4-ethylphenyl | |
| 91) | H | Cl | 2-fluorophenyl | 4-methylphenyl | |
| 92) | H | Cl | 2-fluorophenyl | 2-methylphenyl | |
| 93) | H | Cl | 2-fluorophenyl | 3-methylphenyl | |
| 94) | H | Cl | 2-fluorophenyl | 4-fluorophenyl | |
| 95) | H | Cl | 2-fluorophenyl | 2,4-difluorophenyl | |
| 96) | H | Cl | 2-fluorophenyl | 4-chlorophenyl | |
| 97) | H | Cl | 2-fluorophenyl | 3-chlorophenyl | |
| 98) | H | Cl | 2-fluorophenyl | 2-chlorophenyl | |
| 99) | H | Cl | 2-fluorophenyl | 4-chloro-2-methoxyphenyl | |

TABLE 1-continued

II

| No. | R¹ | R² | Rᵃ | Rᵇ | Phys. Data |
|---|---|---|---|---|---|
| 100) | H | Cl | 2-fluorophenyl | 4-trifluoromethylphenyl | |
| 101) | H | Cl | 2-fluorophenyl | 2-trifluoromethylphenyl | |
| 102) | H | Cl | 2-fluorophenyl | 3-trifluoromethylphenyl | |
| 103) | H | Cl | 2-fluorophenyl | 4-(trifluoromethoxy)phenyl | |
| 104) | H | Cl | 2-fluorophenyl | 3-(trifluoromethoxy)phenyl | |
| 105) | H | Cl | 2-fluorophenyl | 4-(difluoromethoxy)phenyl | |
| 106) | H | Cl | 2-fluorophenyl | 3-(difluoromethoxy)phenyl | |
| 107) | H | Cl | 2-fluorophenyl | 4-cyanophenyl | |
| 108) | H | Cl | 2,4-difluorophenyl | phenyl | |
| 109) | H | Cl | 2,4-difluorophenyl | 4-ethylphenyl | |
| 110) | H | Cl | 2,4-difluorophenyl | 4-methylphenyl | |
| 111) | H | Cl | 2,4-difluorophenyl | 2-methylphenyl | |
| 112) | H | Cl | 2,4-difluorophenyl | 3-methylphenyl | |
| 113) | H | Cl | 2,4-difluorophenyl | 4-fluorophenyl | |
| 114) | H | Cl | 2,4-difluorophenyl | 2,4-difluorophenyl | |
| 115) | H | Cl | 2,4-difluorophenyl | 4-chlorophenyl | |
| 116) | H | Cl | 2,4-difluorophenyl | 3-chlorophenyl | |
| 117) | H | Cl | 2,4-difluorophenyl | 2-chlorophenyl | |
| 118) | H | Cl | 2,4-difluorophenyl | 4-chloro-2-methoxyphenyl | |
| 119) | H | Cl | 2,4-difluorophenyl | 4-trifluoromethylphenyl | |
| 120) | H | Cl | 2,4-difluorophenyl | 2-trifluoromethylphenyl | |
| 121) | H | Cl | 2,4-difluorophenyl | 3-trifluoromethylphenyl | |
| 122) | H | Cl | 2,4-difluorophenyl | 4-(trifluoromethoxy)phenyl | |
| 123) | H | Cl | 2,4-difluorophenyl | 3-(trifluoromethoxy)phenyl | |
| 124) | H | Cl | 2,4-difluorophenyl | 4-(difluoromethoxy)phenyl | |
| 125) | H | Cl | 2,4-difluorophenyl | 3-(difluoromethoxy)phenyl | |
| 126) | H | Cl | 2,4-difluorophenyl | 4-cyanophenyl | |
| 127) | H | Cl | 4-trifluoromethylphenyl | phenyl | m.p. 169–170° C. |
| 128) | H | Cl | 4-trifluoromethylphenyl | 4-ethylphenyl | |
| 129) | H | Cl | 4-trifluoromethylphenyl | 4-methylphenyl | |
| 130) | H | Cl | 4-trifluoromethylphenyl | 2-methylphenyl | |
| 131) | H | Cl | 4-trifluoromethylphenyl | 3-methylphenyl | |
| 132) | H | Cl | 4-trifluoromethylphenyl | 4-fluorophenyl | |
| 133) | H | Cl | 4-trifluoromethylphenyl | 2,4-difluorophenyl | |
| 134) | H | Cl | 4-trifluoromethylphenyl | 4-chlorophenyl | |
| 135) | H | Cl | 4-trifluoromethylphenyl | 3-chlorophenyl | |
| 136) | H | Cl | 4-trifluoromethylphenyl | 2-chlorophenyl | |
| 137) | H | Cl | 4-trifluoromethylphenyl | 4-chloro-2-methoxyphenyl | |
| 138) | H | Cl | 4-trifluoromethylphenyl | 4-trifluoromethylphenyl | |
| 139) | H | Cl | 4-trifluoromethylphenyl | 2-trifluoromethylphenyl | |
| 140) | H | Cl | 4-trifluoromethylphenyl | 3-trifluoromethylphenyl | |
| 141) | H | Cl | 4-trifluoromethylphenyl | 4-(trifluoromethoxy)phenyl | |
| 142) | H | Cl | 4-trifluoromethylphenyl | 3-(trifluoromethoxy)phenyl | |
| 143) | H | Cl | 4-trifluoromethylphenyl | 4-(difluoromethoxy)phenyl | |
| 144) | H | Cl | 4-trifluoromethylphenyl | 3-(difluoromethoxy)phenyl | |
| 145) | H | Cl | 4-trifluoromethylphenyl | 4-cyanophenyl | |
| 146) | H | Cl | 3,4-dichlorophenyl | 4-fluorophenyl | |
| 147) | H | Cl | 3,4-(methylenedioxy)phenyl | phenyl | |
| 148) | H | Cl | 3-trifluoromethylphenyl | phenyl | |
| 149) | H | Cl | 3-trifluoromethylphenyl | 4-ethylphenyl | |
| 150) | H | Cl | 3-trifluoromethylphenyl | 4-methylphenyl | |
| 151) | H | Cl | 3-trifluoromethylphenyl | 2-methylphenyl | |
| 152) | H | Cl | 3-trifluoromethylphenyl | 3-methylphenyl | |
| 153) | H | Cl | 3-trifluoromethylphenyl | 4-fluorophenyl | |
| 154) | H | Cl | 3-trifluoromethylphenyl | 2,4-difluorophenyl | |
| 155) | H | Cl | 3-trifluoromethylphenyl | 4-chlorophenyl | |
| 156) | H | Cl | 3-trifluoromethylphenyl | 3-chlorophenyl | |
| 157) | H | Cl | 3-trifluoromethylphenyl | 2-chlorophenyl | |
| 158) | H | Cl | 3-trifluoromethylphenyl | 4-chloro-2-methoxyphenyl | |
| 159) | H | Cl | 3-trifluoromethylphenyl | 4-trifluoromethylphenyl | |
| 160) | H | Cl | 3-trifluoromethylphenyl | 2-trifluoromethylphenyl | |
| 161) | H | Cl | 3-trifluoromethylphenyl | 3-trifluoromethylphenyl | |
| 162) | H | Cl | 3-trifluoromethylphenyl | 4-(trifluoromethoxy)phenyl | |
| 163) | H | Cl | 3-trifluoromethylphenyl | 3-(trifluoromethoxy)phenyl | |
| 164) | H | Cl | 3-trifluoromethylphenyl | 4-(difluoromethoxy)phenyl | |
| 165) | H | Cl | 3-trifluoromethylphenyl | 3-(difluoromethoxy)phenyl | |
| 166) | H | Cl | 3-trifluoromethylphenyl | 4-cyanophenyl | |

TABLE 1-continued

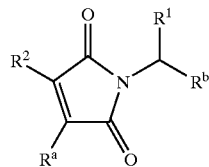

II

| No. | R¹ | R² | Rᵃ | Rᵇ | Phys. Data |
|---|---|---|---|---|---|
| 167) | methyl | Cl | phenyl | phenyl | |
| 168) | methyl | Cl | phenyl | 4-methylphenyl | |
| 169) | methyl | Cl | phenyl | 2,4-dichlorophenyl | |
| 170) | methyl | Cl | 4-methylphenyl | 4-chlorophenyl | |
| 171) | methyl | Cl | 4-methoxyphenyl | 4-methoxyphenyl | |
| 172) | methyl | Cl | 4-methoxyphenyl | 2-methoxyphenyl | |
| 173) | methyl | Cl | 4-methoxyphenyl | 4-chlorophenyl | |
| 174) | methyl | Cl | 4-methoxyphenyl | 2,4-dichlorophenyl | |
| 175) | methyl | Cl | 3-chlorophenyl | phenyl | |
| 176) | methyl | Cl | 3,4-dichlorophenyl | phenyl | |
| 177) | methyl | Cl | 4-chlorophenyl | 4-chlorophenyl | |
| 178) | methyl | Cl | 4-chlorophenyl | 3,4-dichlorophenyl | |
| 179) | methyl | Cl | 4-chlorophenyl | 2,4-dichlorophenyl | |
| 180) | methyl | Cl | 4-chlorophenyl | 4-fluorophenyl | |
| 181) | methyl | Cl | 4-chlorophenyl | 4-methylphenyl | |
| 182) | methyl | Cl | 4-bromophenyl | 4-methoxyphenyl | |
| 183) | methyl | Cl | 4-bromophenyl | 4-methylphenyl | |
| 184) | methyl | Cl | phenyl | 4-isopropylphenyl | |
| 185) | methyl | Cl | phenyl | 4-fluorophenyl | |
| 186) | methyl | Cl | phenyl | 3-fluorophenyl | |
| 187) | methyl | Cl | phenyl | 2-fluorophenyl | |
| 188) | methyl | Cl | phenyl | 2,3,5,6-tetra-fluorophenyl | |
| 189) | methyl | Cl | phenyl | 4-trifluoromethylphenyl | |
| 190) | methyl | Cl | phenyl | 3-trifluoromethylphenyl | |
| 191) | methyl | Cl | phenyl | 4-methylsulfonylphenyl | |
| 192) | methyl | Cl | phenyl | 4-chlorophenyl | |
| 193) | methyl | Cl | phenyl | 3-chlorophenyl | |
| 194) | methyl | Cl | phenyl | 2-chlorophenyl | |
| 195) | methyl | Cl | phenyl | 3,5-dichlorophenyl | |
| 196) | methyl | Cl | phenyl | 4-(trifluoromethoxy)phenyl | |
| 197) | methyl | Cl | phenyl | 3-(trifluoromethoxy)phenyl | |
| 198) | methyl | Cl | phenyl | 4-(difluoromethoxy)phenyl | |
| 199) | methyl | Cl | phenyl | 3-(difluoromethoxy)phenyl | |
| 200) | methyl | Cl | phenyl | 4-cyanophenyl | |
| 201) | methyl | Cl | 4-chlorophenyl | 4-trifluoromethylphenyl | |
| 202) | methyl | Cl | 4-chlorophenyl | 3-trifluoromethylphenyl | |
| 203) | methyl | Cl | 4-chlorophenyl | 2-chlorophenyl | |
| 204) | methyl | Cl | 4-chlorophenyl | 3-chlorophenyl | |
| 205) | methyl | Cl | 4-chlorophenyl | 4-trifluoromethoxyphenyl | |
| 206) | methyl | Cl | 4-chlorophenyl | 3-trifluoromethoxyphenyl | |
| 207) | methyl | Cl | 4-chlorophenyl | 4-difluoromethoxyphenyl | |
| 208) | methyl | Cl | 4-chlorophenyl | 3-difluoromethoxyphenyl | |
| 209) | methyl | Cl | 4-fluorophenyl | phenyl | |
| 210) | methyl | Cl | 4-fluorophenyl | 4-ethylphenyl | |
| 211) | methyl | Cl | 4-fluorophenyl | 4-methylphenyl | |
| 212) | methyl | Cl | 4-fluorophenyl | 2-methylphenyl | |
| 213) | methyl | Cl | 4-fluorophenyl | 3-methylphenyl | |
| 214) | methyl | Cl | 4-fluorophenyl | 4-fluorophenyl | |
| 215) | methyl | Cl | 4-fluorophenyl | 2,4-difluorophenyl | |
| 216) | methyl | Cl | 4-fluorophenyl | 4-chlorophenyl | |
| 217) | methyl | Cl | 4-fluorophenyl | 3-chlorophenyl | |
| 218) | methyl | Cl | 4-fluorophenyl | 2-chlorophenyl | |
| 219) | methyl | Cl | 4-fluorophenyl | 4-chloro-2-methoxyphenyl | |
| 220) | methyl | Cl | 4-fluorophenyl | 4-trifluoromethylphenyl | |
| 221) | methyl | Cl | 4-fluorophenyl | 2-trifluoromethylphenyl | |
| 222) | methyl | Cl | 4-fluorophenyl | 3-trifluoromethylphenyl | |
| 223) | methyl | Cl | 4-fluorophenyl | 4-(trifluoromethoxy)phenyl | |
| 224) | methyl | Cl | 4-fluorophenyl | 3-(trifluoromethoxy)phenyl | |
| 225) | methyl | Cl | 4-fluorophenyl | 4-(difluoromethoxy)phenyl | |
| 226) | methyl | Cl | 4-fluorophenyl | 3-(difluoromethoxy)phenyl | |
| 227) | methyl | Cl | 4-fluorophenyl | 4-cyanophenyl | |
| 228) | methyl | Cl | 3-fluorophenyl | phenyl | |
| 229) | methyl | Cl | 3-fluorophenyl | 4-ethylphenyl | |
| 230) | methyl | Cl | 3-fluorophenyl | 4-methylphenyl | |
| 231) | methyl | Cl | 3-fluorophenyl | 2-methylphenyl | |
| 232) | methyl | Cl | 3-fluorophenyl | 3-methylphenyl | |
| 233) | methyl | Cl | 3-fluorophenyl | 4-fluorophenyl | |

TABLE 1-continued

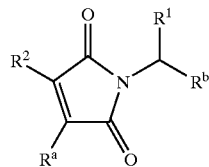

II

| No. | R¹ | R² | Rᵃ | Rᵇ | Phys. Data |
|---|---|---|---|---|---|
| 234) | methyl | Cl | 3-fluorophenyl | 2,4-difluorophenyl | |
| 235) | methyl | Cl | 3-fluorophenyl | 4-chlorophenyl | |
| 236) | methyl | Cl | 3-fluorophenyl | 3-chlorophenyl | |
| 237) | methyl | Cl | 3-fluorophenyl | 2-chlorophenyl | |
| 238) | methyl | Cl | 3-fluorophenyl | 4-chloro-2-methoxyphenyl | |
| 239) | methyl | Cl | 3-fluorophenyl | 4-trifluoromethylphenyl | |
| 240) | methyl | Cl | 3-fluorophenyl | 2-trifluoromethylphenyl | |
| 241) | methyl | Cl | 3-fluorophenyl | 3-trifluoromethylphenyl | |
| 242) | methyl | Cl | 3-fluorophenyl | 4-(trifluoromethoxy)phenyl | |
| 243) | methyl | Cl | 3-fluorophenyl | 3-(trifluoromethoxy)phenyl | |
| 244) | methyl | Cl | 3-fluorophenyl | 4-(difluoromethoxy)phenyl | |
| 245) | methyl | Cl | 3-fluorophenyl | 3-(difluoromethoxy)phenyl | |
| 246) | methyl | Cl | 3-fluorophenyl | 4-cyanophenyl | |
| 247) | methyl | Cl | 2-fluorophenyl | phenyl | |
| 248) | methyl | Cl | 2-fluorophenyl | 4-ethylphenyl | |
| 249) | methyl | Cl | 2-fluorophenyl | 4-methylphenyl | |
| 250) | methyl | Cl | 2-fluorophenyl | 2-methylphenyl | |
| 251) | methyl | Cl | 2-fluorophenyl | 3-methylphenyl | |
| 252) | methyl | Cl | 2-fluorophenyl | 4-fluorophenyl | |
| 253) | methyl | Cl | 2-fluorophenyl | 2,4-difluorophenyl | |
| 254) | methyl | Cl | 2-fluorophenyl | 4-chlorophenyl | |
| 255) | methyl | Cl | 2-fluorophenyl | 3-chlorophenyl | |
| 256) | methyl | Cl | 2-fluorophenyl | 2-chlorophenyl | |
| 257) | methyl | Cl | 2-fluorophenyl | 4-chloro-2-methoxyphenyl | |
| 258) | methyl | Cl | 2-fluorophenyl | 4-trifluoromethylphenyl | |
| 259) | methyl | Cl | 2-fluorophenyl | 2-trifluoromethylphenyl | |
| 260) | methyl | Cl | 2-fluorophenyl | 3-trifluoromethylphenyl | |
| 261) | methyl | Cl | 2-fluorophenyl | 4-(trifluoromethoxy)phenyl | |
| 262) | methyl | Cl | 2-fluorophenyl | 3-(trifluoromethoxy)phenyl | |
| 263) | methyl | Cl | 2-fluorophenyl | 4-(difluoromethoxy)phenyl | |
| 264) | methyl | Cl | 2-fluorophenyl | 3-(difluoromethoxy)phenyl | |
| 265) | methyl | Cl | 2-fluorophenyl | 4-cyanophenyl | |
| 266) | methyl | Cl | 2,4-difluorophenyl | phenyl | |
| 267) | methyl | Cl | 2,4-difluorophenyl | 4-ethylphenyl | |
| 268) | methyl | Cl | 2,4-difluorophenyl | 4-methylphenyl | |
| 269) | methyl | Cl | 2,4-difluorophenyl | 2-methylphenyl | |
| 270) | methyl | Cl | 2,4-difluorophenyl | 3-methylphenyl | |
| 271) | methyl | Cl | 2,4-difluorophenyl | 4-fluorophenyl | |
| 272) | methyl | Cl | 2,4-difluorophenyl | 2,4-difluorophenyl | |
| 273) | methyl | Cl | 2,4-difluorophenyl | 4-chlorophenyl | |
| 274) | methyl | Cl | 2,4-difluorophenyl | 3-chlorophenyl | |
| 275) | methyl | Cl | 2,4-difluorophenyl | 2-chlorophenyl | |
| 276) | methyl | Cl | 2,4-difluorophenyl | 4-chloro-2-methoxyphenyl | |
| 277) | methyl | Cl | 2,4-difluorophenyl | 4-trifluoromethylphenyl | |
| 278) | methyl | Cl | 2,4-difluorophenyl | 2-trifluoromethylphenyl | |
| 279) | methyl | Cl | 2,4-difluorophenyl | 3-trifluoromethylphenyl | |
| 280) | methyl | Cl | 2,4-difluorophenyl | 4-(trifluoromethoxy)phenyl | |
| 281) | methyl | Cl | 2,4-difluorophenyl | 3-(trifluoromethoxy)phenyl | |
| 282) | methyl | Cl | 2,4-difluorophenyl | 4-(difluoromethoxy)phenyl | |
| 283) | methyl | Cl | 2,4-difluorophenyl | 3-(difluoromethoxy)phenyl | |
| 284) | methyl | Cl | 2,4-difluorophenyl | 4-cyanophenyl | |
| 285) | methyl | Cl | 4-trifluoromethylphenyl | phenyl | |
| 286) | methyl | Cl | 4-trifluoromethylphenyl | 4-ethylphenyl | |
| 287) | methyl | Cl | 4-trifluoromethylphenyl | 4-methylphenyl | |
| 288) | methyl | Cl | 4-trifluoromethylphenyl | 2-methylphenyl | |
| 289) | methyl | Cl | 4-trifluoromethylphenyl | 3-methylphenyl | |
| 290) | methyl | Cl | 4-trifluoromethylphenyl | 4-fluorophenyl | |
| 291) | methyl | Cl | 4-trifluoromethylphenyl | 2,4-difluorophenyl | |
| 292) | methyl | Cl | 4-trifluoromethylphenyl | 4-chlorophenyl | |
| 293) | methyl | Cl | 4-trifluoromethylphenyl | 3-chlorophenyl | |
| 294) | methyl | Cl | 4-trifluoromethylphenyl | 2-chlorophenyl | |
| 295) | methyl | Cl | 4-trifluoromethylphenyl | 4-chloro-2-methoxyphenyl | |
| 296) | methyl | Cl | 4-trifluoromethylphenyl | 4-trifluoromethylphenyl | |
| 297) | methyl | Cl | 4-trifluoromethylphenyl | 2-trifluoromethylphenyl | |
| 298) | methyl | Cl | 4-trifluoromethylphenyl | 3-trifluoromethylphenyl | |
| 299) | methyl | Cl | 4-trifluoromethylphenyl | 4-(trifluoromethoxy)phenyl | |
| 300) | methyl | Cl | 4-trifluoromethylphenyl | 3-(trifluoromethoxy)phenyl | |

TABLE 1-continued

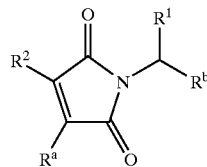

II

| No. | R¹ | R² | Rᵃ | Rᵇ | Phys. Data |
|---|---|---|---|---|---|
| 301) | methyl | Cl | 4-trifluoromethylphenyl | 4-(difluoromethoxy)phenyl | |
| 302) | methyl | Cl | 4-trifluoromethylphenyl | 3-(difluoromethoxy)phenyl | |
| 303) | methyl | Cl | 4-trifluoromethylphenyl | 4-cyanophenyl | |
| 304) | methyl | Cl | 3,4-dichlorophenyl | 4-fluorophenyl | |
| 305) | methyl | Cl | 3,4-(methylenedioxy)-phenyl | phenyl | |
| 306) | methyl | Cl | 3-trifluoromethylphenyl | phenyl | |
| 307) | methyl | Cl | 3-trifluoromethylphenyl | 4-ethylphenyl | |
| 308) | methyl | Cl | 3-trifluoromethylphenyl | 4-methylphenyl | |
| 309) | methyl | Cl | 3-trifluoromethylphenyl | 2-methylphenyl | |
| 310) | methyl | Cl | 3-trifluoromethylphenyl | 3-methylphenyl | |
| 311) | methyl | Cl | 3-trifluoromethylphenyl | 4-fluorophenyl | |
| 312) | methyl | Cl | 3-trifluoromethylphenyl | 2,4-difluorophenyl | |
| 313) | methyl | Cl | 3-trifluoromethylphenyl | 4-chlorophenyl | |
| 314) | methyl | Cl | 3-trifluoromethylphenyl | 3-chlorophenyl | |
| 315) | methyl | Cl | 3-trifluoromethylphenyl | 2-chlorophenyl | |
| 316) | methyl | Cl | 3-trifluoromethylphenyl | 4-chloro-2-methoxyphenyl | |
| 317) | methyl | Cl | 3-trifluoromethylphenyl | 4-trifluoromethylphenyl | |
| 318) | methyl | Cl | 3-trifluoromethylphenyl | 2-trifluoromethylphenyl | |
| 319) | methyl | Cl | 3-trifluoromethylphenyl | 3-trifluoromethylphenyl | |
| 320) | methyl | Cl | 3-trifluoromethylphenyl | 4-(trifluoromethoxy)phenyl | |
| 321) | methyl | Cl | 3-trifluoromethylphenyl | 3-(trifluoromethoxy)phenyl | |
| 322) | methyl | Cl | 3-trifluoromethylphenyl | 4-(difluoromethoxy)phenyl | |
| 323) | methyl | Cl | 3-trifluoromethylphenyl | 3-(difluoromethoxy)phenyl | |
| 324) | methyl | Cl | 3-trifluoromethylphenyl | 4-cyanophenyl | |
| 325) | formyl | Cl | phenyl | phenyl | |
| 326) | formyl | Cl | phenyl | 4-methylphenyl | |
| 327) | formyl | Cl | phenyl | 2,4-dichlorophenyl | |
| 328) | formyl | Cl | 4-methylphenyl | 4-chlorophenyl | |
| 329) | formyl | Cl | 4-methoxyphenyl | 4-methoxyphenyl | |
| 330) | formyl | Cl | 4-methoxyphenyl | 2-methoxyphenyl | |
| 331) | formyl | Cl | 4-methoxyphenyl | 4-chlorophenyl | |
| 332) | formyl | Cl | 4-methoxyphenyl | 2,4-dichlorophenyl | |
| 333) | formyl | Cl | 3-chlorophenyl | phenyl | |
| 334) | formyl | Cl | 3,4-dichlorophenyl | phenyl | |
| 335) | formyl | Cl | 4-chlorophenyl | 4-chlorophenyl | |
| 336) | formyl | Cl | 4-chlorophenyl | 3,4-dichlorophenyl | |
| 337) | formyl | Cl | 4-chlorophenyl | 2,4-dichlorophenyl | |
| 338) | formyl | Cl | 4-chlorophenyl | 4-fluorophenyl | |
| 339) | formyl | Cl | 4-chlorophenyl | 4-formylphenyl | |
| 340) | formyl | Cl | 4-bromophenyl | 4-methoxyphenyl | |
| 341) | formyl | Cl | 4-bromophenyl | 4-formylphenyl | |
| 342) | formyl | Cl | phenyl | 4-isopropylphenyl | |
| 343) | formyl | Cl | phenyl | 4-fluorophenyl | |
| 344) | formyl | Cl | phenyl | 3-fluorophenyl | |
| 345) | formyl | Cl | phenyl | 2-fluorophenyl | |
| 346) | formyl | Cl | phenyl | 2,3,5,6-tetra-fluorophenyl | |
| 347) | formyl | Cl | phenyl | 4-trifluoromethylphenyl | |
| 348) | formyl | Cl | phenyl | 3-trifluoromethylphenyl | |
| 349) | formyl | Cl | phenyl | 4-formylsulfonylphenyl | |
| 350) | formyl | Cl | phenyl | 4-chlorophenyl | |
| 351) | formyl | Cl | phenyl | 3-chlorophenyl | |
| 352) | formyl | Cl | phenyl | 2-chlorophenyl | |
| 353) | formyl | Cl | phenyl | 3,5-dichlorophenyl | |
| 354) | formyl | Cl | phenyl | 4-(trifluoromethoxy)phenyl | |
| 355) | formyl | Cl | phenyl | 3-(trifluoromethoxy)phenyl | |
| 356) | formyl | Cl | phenyl | 4-(difluoromethoxy)phenyl | |
| 357) | formyl | Cl | phenyl | 3-(difluoromethoxy)phenyl | |
| 358) | formyl | Cl | phenyl | 4-cyanophenyl | |
| 359) | formyl | Cl | 4-chlorophenyl | 4-trifluoromethylphenyl | |
| 360) | formyl | Cl | 4-chlorophenyl | 3-trifluoromethylphenyl | |
| 361) | formyl | Cl | 4-chlorophenyl | 2-chlorophenyl | |
| 362) | formyl | Cl | 4-chlorophenyl | 3-chlorophenyl | |
| 363) | formyl | Cl | 4-chlorophenyl | 4-trifluoromethoxyphenyl | |
| 364) | formyl | Cl | 4-chlorophenyl | 3-trifluoromethoxyphenyl | |
| 365) | formyl | Cl | 4-chlorophenyl | 4-difluoromethoxyphenyl | |
| 366) | formyl | Cl | 4-chlorophenyl | 3-difluoromethoxyphenyl | |
| 367) | formyl | Cl | 4-fluorophenyl | phenyl | |

TABLE 1-continued

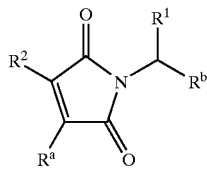

II

| No. | R¹ | R² | Rᵃ | Rᵇ | Phys. Data |
|---|---|---|---|---|---|
| 368) | formyl | Cl | 4-fluorophenyl | 4-ethylphenyl | |
| 369) | formyl | Cl | 4-fluorophenyl | 4-formylphenyl | |
| 370) | formyl | Cl | 4-fluorophenyl | 2-formylphenyl | |
| 371) | formyl | Cl | 4-fluorophenyl | 3-formylphenyl | |
| 372) | formyl | Cl | 4-fluorophenyl | 4-fluorophenyl | |
| 373) | formyl | Cl | 4-fluorophenyl | 2,4-difluorophenyl | |
| 374) | formyl | Cl | 4-fluorophenyl | 4-chlorophenyl | |
| 375) | formyl | Cl | 4-fluorophenyl | 3-chlorophenyl | |
| 376) | formyl | Cl | 4-fluorophenyl | 2-chlorophenyl | |
| 377) | formyl | Cl | 4-fluorophenyl | 4-chloro-2-methoxyphenyl | |
| 378) | formyl | Cl | 4-fluorophenyl | 4-trifluoromethylphenyl | |
| 379) | formyl | Cl | 4-fluorophenyl | 2-trifluoromethylphenyl | |
| 380) | formyl | Cl | 4-fluorophenyl | 3-trifluoromethylphenyl | |
| 381) | formyl | Cl | 4-fluorophenyl | 4-(trifluoromethoxy)phenyl | |
| 382) | formyl | Cl | 4-fluorophenyl | 3-(trifluoromethoxy)phenyl | |
| 383) | formyl | Cl | 4-fluorophenyl | 4-(difluoromethoxy)phenyl | |
| 384) | formyl | Cl | 4-fluorophenyl | 3-(difluoromethoxy)phenyl | |
| 385) | formyl | Cl | 4-fluorophenyl | 4-cyanophenyl | |
| 386) | formyl | Cl | 3-fluorophenyl | phenyl | |
| 387) | formyl | Cl | 3-fluorophenyl | 4-ethylphenyl | |
| 388) | formyl | Cl | 3-fluorophenyl | 4-formylphenyl | |
| 389) | formyl | Cl | 3-fluorophenyl | 2-formylphenyl | |
| 390) | formyl | Cl | 3-fluorophenyl | 3-formylphenyl | |
| 391) | formyl | Cl | 3-fluorophenyl | 4-fluorophenyl | |
| 392) | formyl | Cl | 3-fluorophenyl | 2,4-difluorophenyl | |
| 393) | formyl | Cl | 3-fluorophenyl | 4-chlorophenyl | |
| 394) | formyl | Cl | 3-fluorophenyl | 3-chlorophenyl | |
| 395) | formyl | Cl | 3-fluorophenyl | 2-chlorophenyl | |
| 396) | formyl | Cl | 3-fluorophenyl | 4-chloro-2-methoxyphenyl | |
| 397) | formyl | Cl | 3-fluorophenyl | 4-trifluoromethylphenyl | |
| 398) | formyl | Cl | 3-fluorophenyl | 2-trifluoromethylphenyl | |
| 399) | formyl | Cl | 3-fluorophenyl | 3-trifluoromethylphenyl | |
| 400) | formyl | Cl | 3-fluorophenyl | 4-(trifluoromethoxy)phenyl | |
| 401) | formyl | Cl | 3-fluorophenyl | 3-(trifluoromethoxy)phenyl | |
| 402) | formyl | Cl | 3-fluorophenyl | 4-(difluoromethoxy)phenyl | |
| 403) | formyl | Cl | 3-fluorophenyl | 3-(difluoromethoxy)phenyl | |
| 404) | formyl | Cl | 3-fluorophenyl | 4-cyanophenyl | |
| 405) | formyl | Cl | 2-fluorophenyl | phenyl | |
| 406) | formyl | Cl | 2-fluorophenyl | 4-ethylphenyl | |
| 407) | formyl | Cl | 2-fluorophenyl | 4-formylphenyl | |
| 408) | formyl | Cl | 2-fluorophenyl | 2-formylphenyl | |
| 409) | formyl | Cl | 2-fluorophenyl | 3-formylphenyl | |
| 410) | formyl | Cl | 2-fluorophenyl | 4-fluorophenyl | |
| 411) | formyl | Cl | 2-fluorophenyl | 2,4-difluorophenyl | |
| 412) | formyl | Cl | 2-fluorophenyl | 4-chlorophenyl | |
| 413) | formyl | Cl | 2-fluorophenyl | 3-chlorophenyl | |
| 414) | formyl | Cl | 2-fluorophenyl | 2-chlorophenyl | |
| 415) | formyl | Cl | 2-fluorophenyl | 4-chloro-2-methoxyphenyl | |
| 416) | formyl | Cl | 2-fluorophenyl | 4-trifluoromethylphenyl | |
| 417) | formyl | Cl | 2-fluorophenyl | 2-trifluoromethylphenyl | |
| 418) | formyl | Cl | 2-fluorophenyl | 3-trifluoromethylphenyl | |
| 419) | formyl | Cl | 2-fluorophenyl | 4-(trifluoromethoxy)phenyl | |
| 420) | formyl | Cl | 2-fluorophenyl | 3-(trifluoromethoxy)phenyl | |
| 421) | formyl | Cl | 2-fluorophenyl | 4-(difluoromethoxy)phenyl | |
| 422) | formyl | Cl | 2-fluorophenyl | 3-(difluoromethoxy)phenyl | |
| 423) | formyl | Cl | 2-fluorophenyl | 4-cyanophenyl | |
| 424) | formyl | Cl | 2,4-difluorophenyl | phenyl | |
| 425) | formyl | Cl | 2,4-difluorophenyl | 4-ethylphenyl | |
| 426) | formyl | Cl | 2,4-difluorophenyl | 4-formylphenyl | |
| 427) | formyl | Cl | 2,4-difluorophenyl | 2-formylphenyl | |
| 428) | formyl | Cl | 2,4-difluorophenyl | 3-formylphenyl | |
| 429) | formyl | Cl | 2,4-difluorophenyl | 4-fluorophenyl | |
| 430) | formyl | Cl | 2,4-difluorophenyl | 2,4-difluorophenyl | |
| 431) | formyl | Cl | 2,4-difluorophenyl | 4-chlorophenyl | |
| 432) | formyl | Cl | 2,4-difluorophenyl | 3-chlorophenyl | |
| 433) | formyl | Cl | 2,4-difluorophenyl | 2-chlorophenyl | |
| 434) | formyl | Cl | 2,4-difluorophenyl | 4-chloro-2-methoxyphenyl | |

TABLE 1-continued

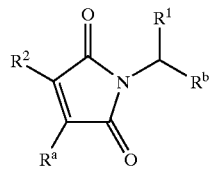

| No. | R¹ | R² | Rᵃ | Rᵇ | Phys. Data |
|---|---|---|---|---|---|
| 435) | formyl | Cl | 2,4-difluorophenyl | 4-trifluoromethylphenyl | |
| 436) | formyl | Cl | 2,4-difluorophenyl | 2-trifluoromethylphenyl | |
| 437) | formyl | Cl | 2,4-difluorophenyl | 3-trifluoromethylphenyl | |
| 438) | formyl | Cl | 2,4-difluorophenyl | 4-(trifluoromethoxy)phenyl | |
| 439) | formyl | Cl | 2,4-difluorophenyl | 3-(trifluoromethoxy)phenyl | |
| 440) | formyl | Cl | 2,4-difluorophenyl | 4-(difluoromethoxy)phenyl | |
| 441) | formyl | Cl | 2,4-difluorophenyl | 3-(difluoromethoxy)phenyl | |
| 442) | formyl | Cl | 2,4-difluorophenyl | 4-cyanophenyl | |
| 443) | formyl | Cl | 4-trifluoromethylphenyl | phenyl | |
| 444) | formyl | Cl | 4-trifluoromethylphenyl | 4-ethylphenyl | |
| 445) | formyl | Cl | 4-trifluoromethylphenyl | 4-formylphenyl | |
| 446) | formyl | Cl | 4-trifluoromethylphenyl | 2-formylphenyl | |
| 447) | formyl | Cl | 4-trifluoromethylphenyl | 3-formylphenyl | |
| 448) | formyl | Cl | 4-trifluoromethylphenyl | 4-fluorophenyl | |
| 449) | formyl | Cl | 4-trifluoromethylphenyl | 2,4-difluorophenyl | |
| 450) | formyl | Cl | 4-trifluoromethylphenyl | 4-chlorophenyl | |
| 451) | formyl | Cl | 4-trifluoromethylphenyl | 3-chlorophenyl | |
| 452) | formyl | Cl | 4-trifluoromethylphenyl | 2-chlorophenyl | |
| 453) | formyl | Cl | 4-trifluoromethylphenyl | 4-chloro-2-methoxyphenyl | |
| 454) | formyl | Cl | 4-trifluoromethylphenyl | 4-trifluoromethylphenyl | |
| 455) | formyl | Cl | 4-trifluoromethylphenyl | 2-trifluoromethylphenyl | |
| 456) | formyl | Cl | 4-trifluoromethylphenyl | 3-trifluoromethylphenyl | |
| 457) | formyl | Cl | 4-trifluoromethylphenyl | 4-(trifluoromethoxy)phenyl | |
| 458) | formyl | Cl | 4-trifluoromethylphenyl | 3-(trifluoromethoxy)phenyl | |
| 459) | formyl | Cl | 4-trifluoromethylphenyl | 4-(difluoromethoxy)phenyl | |
| 460) | formyl | Cl | 4-trifluoromethylphenyl | 3-(difluoromethoxy)phenyl | |
| 461) | formyl | Cl | 4-trifluoromethylphenyl | 4-cyanophenyl | |
| 462) | formyl | Cl | 3,4-dichlorophenyl | 4-fluorophenyl | |
| 463) | formyl | Cl | 3,4-(formylenedioxy)phenyl | phenyl | |
| 464) | formyl | Cl | 3-trifluoromethylphenyl | phenyl | |
| 465) | formyl | Cl | 3-trifluoromethylphenyl | 4-ethylphenyl | |
| 466) | formyl | Cl | 3-trifluoromethylphenyl | 4-formylphenyl | |
| 467) | formyl | Cl | 3-trifluoromethylphenyl | 2-formylphenyl | |
| 468) | formyl | Cl | 3-trifluoromethylphenyl | 3-formylphenyl | |
| 469) | formyl | Cl | 3-trifluoromethylphenyl | 4-fluorophenyl | |
| 470) | formyl | Cl | 3-trifluoromethylphenyl | 2,4-difluorophenyl | |
| 471) | formyl | Cl | 3-trifluoromethylphenyl | 4-chlorophenyl | |
| 472) | formyl | Cl | 3-trifluoromethylphenyl | 3-chlorophenyl | |
| 473) | formyl | Cl | 3-trifluoromethylphenyl | 2-chlorophenyl | |
| 474) | formyl | Cl | 3-trifluoromethylphenyl | 4-chloro-2-methoxyphenyl | |
| 475) | formyl | Cl | 3-trifluoromethylphenyl | 4-trifluoromethylphenyl | |
| 476) | formyl | Cl | 3-trifluoromethylphenyl | 2-trifluoromethylphenyl | |
| 477) | formyl | Cl | 3-trifluoromethylphenyl | 3-trifluoromethylphenyl | |
| 478) | formyl | Cl | 3-trifluoromethylphenyl | 4-(trifluoromethoxy)phenyl | |
| 479) | formyl | Cl | 3-trifluoromethylphenyl | 3-(trifluoromethoxy)phenyl | |
| 480) | formyl | Cl | 3-trifluoromethylphenyl | 4-(difluoromethoxy)phenyl | |
| 481) | formyl | Cl | 3-trifluoromethylphenyl | 3-(difluoromethoxy)phenyl | |
| 482) | formyl | Cl | 3-trifluoromethylphenyl | 4-cyanophenyl | |
| 483) | formyl | Cl | 4-formylphenyl | phenyl | |
| 484) | formyl | Cl | 4-methoxyphenyl | phenyl | |
| 485) | formyl | Cl | 4-chlorophenyl | phenyl | |
| 486) | H | Br | phenyl | phenyl | m.p. 146–147° C. |
| 487) | H | Br | phenyl | 4-methylphenyl | |
| 488) | H | Br | phenyl | 2,4-dichlorophenyl | |
| 489) | H | Br | 4-methylphenyl | phenyl | |
| 490) | H | Br | 4-methylphenyl | 4-chlorophenyl | |
| 491) | H | Br | 4-methoxyphenyl | phenyl | |
| 492) | H | Br | 4-methoxyphenyl | 4-methoxyphenyl | |
| 493) | H | Br | 4-methoxyphenyl | 2-methoxyphenyl | |
| 494) | H | Br | 4-methoxyphenyl | 4-chlorophenyl | |
| 495) | H | Br | 4-methoxyphenyl | 2,4-dichlorophenyl | |
| 496) | H | Br | 3-chlorophenyl | phenyl | |
| 497) | H | Br | 3,4-dichlorophenyl | phenyl | |
| 498) | H | Br | 4-chlorophenyl | phenyl | |
| 499) | H | Br | 4-chlorophenyl | 4-chlorophenyl | |
| 500) | H | Br | 4-chlorophenyl | 3,4-dichlorophenyl | |
| 501) | H | Br | 4-chlorophenyl | 2,4-dichlorophenyl | |

TABLE 1-continued

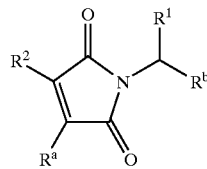

II

| No. | R¹ | R² | Rᵃ | Rᵇ | Phys. Data |
|---|---|---|---|---|---|
| 502) | H | Br | 4-chlorophenyl | 4-fluorophenyl | |
| 503) | H | Br | 4-chlorophenyl | 4-methylphenyl | |
| 504) | H | Br | 4-bromophenyl | 4-methoxyphenyl | |
| 505) | H | Br | 4-bromophenyl | 4-methylphenyl | |
| 506) | methyl | Br | 4-methylphenyl | phenyl | |
| 507) | methyl | Br | 4-methoxyphenyl | phenyl | |
| 508) | methyl | Br | 4-chlorophenyl | phenyl | |
| 509) | H | Br | phenyl | 4-isopropylphenyl | |
| 510) | H | Br | phenyl | 4-fluorophenyl | |
| 511) | H | Br | phenyl | 3-fluorophenyl | |
| 512) | H | Br | phenyl | 2-fluorophenyl | |
| 513) | H | Br | phenyl | 2,3,5,6-tetra-fluorophenyl | |
| 514) | H | Br | phenyl | 4-trifluoromethylphenyl | |
| 515) | H | Br | phenyl | 3-trifluoromethylphenyl | |
| 516) | H | Br | phenyl | 4-methylsulfonylphenyl | |
| 517) | H | Br | phenyl | 4-chlorophenyl | |
| 518) | H | Br | phenyl | 3-chlorophenyl | |
| 519) | H | Br | phenyl | 2-chlorophenyl | |
| 520) | H | Br | phenyl | 3,5-dichlorophenyl | |
| 521) | H | Br | phenyl | 4-(trifluoromethoxy)phenyl | |
| 522) | H | Br | phenyl | 3-(trifluoromethoxy)phenyl | |
| 523) | H | Br | phenyl | 4-(difluoromethoxy)phenyl | |
| 524) | H | Br | phenyl | 3-(difluoromethoxy)phenyl | |
| 525) | H | Br | phenyl | 4-cyanophenyl | |
| 526) | H | Br | 4-chlorophenyl | 4-trifluoromethylphenyl | |
| 527) | H | Br | 4-chlorophenyl | 3-trifluoromethylphenyl | |
| 528) | H | Br | 4-chlorophenyl | 2-chlorophenyl | |
| 529) | H | Br | 4-chlorophenyl | 3-chlorophenyl | |
| 530) | H | Br | 4-chlorophenyl | 4-trifluoromethoxyphenyl | |
| 531) | H | Br | 4-chlorophenyl | 3-trifluoromethoxyphenyl | |
| 532) | H | Br | 4-chlorophenyl | 4-difluoromethoxyphenyl | |
| 533) | H | Br | 4-chlorophenyl | 3-difluoromethoxyphenyl | |
| 534) | H | Br | 4-fluorophenyl | phenyl | |
| 535) | H | Br | 4-fluorophenyl | 4-ethylphenyl | |
| 536) | H | Br | 4-fluorophenyl | 4-methylphenyl | |
| 537) | H | Br | 4-fluorophenyl | 2-methylphenyl | |
| 538) | H | Br | 4-fluorophenyl | 3-methylphenyl | |
| 539) | H | Br | 4-fluorophenyl | 4-fluorophenyl | |
| 540) | H | Br | 4-fluorophenyl | 2,4-difluorophenyl | |
| 541) | H | Br | 4-fluorophenyl | 4-chlorophenyl | |
| 542) | H | Br | 4-fluorophenyl | 3-chlorophenyl | |
| 543) | H | Br | 4-fluorophenyl | 2-chlorophenyl | |
| 544) | H | Br | 4-fluorophenyl | 4-chloro-2-methoxyphenyl | |
| 545) | H | Br | 4-fluorophenyl | 4-trifluoromethylphenyl | |
| 546) | H | Br | 4-fluorophenyl | 2-trifluoromethylphenyl | |
| 547) | H | Br | 4-fluorophenyl | 3-trifluoromethylphenyl | |
| 548) | H | Br | 4-fluorophenyl | 4-(trifluoromethoxy)phenyl | |
| 549) | H | Br | 4-fluorophenyl | 3-(trifluoromethoxy)phenyl | |
| 550) | H | Br | 4-fluorophenyl | 4-(difluoromethoxy)phenyl | |
| 551) | H | Br | 4-fluorophenyl | 3-(difluoromethoxy)phenyl | |
| 552) | H | Br | 4-fluorophenyl | 4-cyanophenyl | |
| 553) | H | Br | 3-fluorophenyl | phenyl | |
| 554) | H | Br | 3-fluorophenyl | 4-ethylphenyl | |
| 555) | H | Br | 3-fluorophenyl | 4-methylphenyl | |
| 556) | H | Br | 3-fluorophenyl | 2-methylphenyl | |
| 557) | H | Br | 3-fluorophenyl | 3-methylphenyl | |
| 558) | H | Br | 3-fluorophenyl | 4-fluorophenyl | |
| 559) | H | Br | 3-fluorophenyl | 2,4-difluorophenyl | |
| 560) | H | Br | 3-fluorophenyl | 4-chlorophenyl | |
| 561) | H | Br | 3-fluorophenyl | 3-chlorophenyl | |
| 562) | H | Br | 3-fluorophenyl | 2-chlorophenyl | |
| 563) | H | Br | 3-fluorophenyl | 4-chloro-2-methoxyphenyl | |
| 564) | H | Br | 3-fluorophenyl | 4-trifluoromethylphenyl | |
| 565) | H | Br | 3-fluorophenyl | 2-trifluoromethylphenyl | |
| 566) | H | Br | 3-fluorophenyl | 3-trifluoromethylphenyl | |
| 567) | H | Br | 3-fluorophenyl | 4-(trifluoromethoxy)phenyl | |
| 568) | H | Br | 3-fluorophenyl | 3-(trifluoromethoxy)phenyl | |

TABLE 1-continued

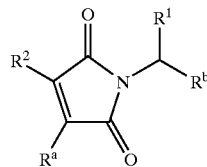

II

| No. | R¹ | R² | Rᵃ | Rᵇ | Phys. Data |
|---|---|---|---|---|---|
| 569) | H | Br | 3-fluorophenyl | 4-(difluoromethoxy)phenyl | |
| 570) | H | Br | 3-fluorophenyl | 3-(difluoromethoxy)phenyl | |
| 571) | H | Br | 3-fluorophenyl | 4-cyanophenyl | |
| 572) | H | Br | 2-fluorophenyl | phenyl | |
| 573) | H | Br | 2-fluorophenyl | 4-ethylphenyl | |
| 574) | H | Br | 2-fluorophenyl | 4-methylphenyl | |
| 575) | H | Br | 2-fluorophenyl | 2-methylphenyl | |
| 576) | H | Br | 2-fluorophenyl | 3-methylphenyl | |
| 577) | H | Br | 2-fluorophenyl | 4-fluorophenyl | |
| 578) | H | Br | 2-fluorophenyl | 2,4-difluorophenyl | |
| 579) | H | Br | 2-fluorophenyl | 4-chlorophenyl | |
| 580) | H | Br | 2-fluorophenyl | 3-chlorophenyl | |
| 581) | H | Br | 2-fluorophenyl | 2-chlorophenyl | |
| 582) | H | Br | 2-fluorophenyl | 4-chloro-2-methoxyphenyl | |
| 583) | H | Br | 2-fluorophenyl | 4-trifluoromethylphenyl | |
| 584) | H | Br | 2-fluorophenyl | 2-trifluoromethylphenyl | |
| 585) | H | Br | 2-fluorophenyl | 3-trifluoromethylphenyl | |
| 586) | H | Br | 2-fluorophenyl | 4-(trifluoromethoxy)phenyl | |
| 587) | H | Br | 2-fluorophenyl | 3-(trifluoromethoxy)phenyl | |
| 588) | H | Br | 2-fluorophenyl | 4-(difluoromethoxy)phenyl | |
| 589) | H | Br | 2-fluorophenyl | 3-(difluoromethoxy)phenyl | |
| 590) | H | Br | 2-fluorophenyl | 4-cyanophenyl | |
| 591) | H | Br | 2,4-difluorophenyl | phenyl | |
| 592) | H | Br | 2,4-difluorophenyl | 4-ethylphenyl | |
| 593) | H | Br | 2,4-difluorophenyl | 4-methylphenyl | |
| 594) | H | Br | 2,4-difluorophenyl | 2-methylphenyl | |
| 595) | H | Br | 2,4-difluorophenyl | 3-methylphenyl | |
| 596) | H | Br | 2,4-difluorophenyl | 4-fluorophenyl | |
| 597) | H | Br | 2,4-difluorophenyl | 2,4-difluorophenyl | |
| 598) | H | Br | 2,4-difluorophenyl | 4-chlorophenyl | |
| 599) | H | Br | 2,4-difluorophenyl | 3-chlorophenyl | |
| 600) | H | Br | 2,4-difluorophenyl | 2-chlorophenyl | |
| 601) | H | Br | 2,4-difluorophenyl | 4-chloro-2-methoxyphenyl | |
| 602) | H | Br | 2,4-difluorophenyl | 4-trifluoromethylphenyl | |
| 603) | H | Br | 2,4-difluorophenyl | 2-trifluoromethylphenyl | |
| 604) | H | Br | 2,4-difluorophenyl | 3-trifluoromethylphenyl | |
| 605) | H | Br | 2,4-difluorophenyl | 4-(trifluoromethoxy)phenyl | |
| 606) | H | Br | 2,4-difluorophenyl | 3-(trifluoromethoxy)phenyl | |
| 607) | H | Br | 2,4-difluorophenyl | 4-(difluoromethoxy)phenyl | |
| 608) | H | Br | 2,4-difluorophenyl | 3-(difluoromethoxy)phenyl | |
| 609) | H | Br | 2,4-difluorophenyl | 4-cyanophenyl | |
| 610) | H | Br | 4-trifluoromethylphenyl | phenyl | |
| 611) | H | Br | 4-trifluoromethylphenyl | 4-ethylphenyl | |
| 612) | H | Br | 4-trifluoromethylphenyl | 4-methylphenyl | |
| 613) | H | Br | 4-trifluoromethylphenyl | 2-methylphenyl | |
| 614) | H | Br | 4-trifluoromethylphenyl | 3-methylphenyl | |
| 615) | H | Br | 4-trifluoromethylphenyl | 4-fluorophenyl | |
| 616) | H | Br | 4-trifluoromethylphenyl | 2,4-difluorophenyl | |
| 617) | H | Br | 4-trifluoromethylphenyl | 4-chlorophenyl | |
| 618) | H | Br | 4-trifluoromethylphenyl | 3-chlorophenyl | |
| 619) | H | Br | 4-trifluoromethylphenyl | 2-chlorophenyl | |
| 620) | H | Br | 4-trifluoromethylphenyl | 4-chloro-2-methoxyphenyl | |
| 621) | H | Br | 4-trifluoromethylphenyl | 4-trifluoromethylphenyl | |
| 622) | H | Br | 4-trifluoromethylphenyl | 2-trifluoromethylphenyl | |
| 623) | H | Br | 4-trifluoromethylphenyl | 3-trifluoromethylphenyl | |
| 624) | H | Br | 4-trifluoromethylphenyl | 4-(trifluoromethoxy)phenyl | |
| 625) | H | Br | 4-trifluoromethylphenyl | 3-(trifluoromethoxy)phenyl | |
| 626) | H | Br | 4-trifluoromethylphenyl | 4-(difluoromethoxy)phenyl | |
| 627) | H | Br | 4-trifluoromethylphenyl | 3-(difluoromethoxy)phenyl | |
| 628) | H | Br | 4-trifluoromethylphenyl | 4-cyanophenyl | |
| 629) | H | Br | 3,4-dichlorophenyl | 4-fluorophenyl | |
| 630) | H | Br | 3,4-(methylenedioxy)phenyl | phenyl | |
| 631) | H | Br | 3-trifluoromethylphenyl | phenyl | |
| 632) | H | Br | 3-trifluoromethylphenyl | 4-ethylphenyl | |
| 633) | H | Br | 3-trifluoromethylphenyl | 4-methylphenyl | |
| 634) | H | Br | 3-trifluoromethylphenyl | 2-methylphenyl | |
| 635) | H | Br | 3-trifluoromethylphenyl | 3-methylphenyl | |

TABLE 1-continued

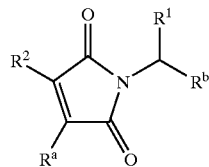

| No. | R¹ | R² | Rᵃ | Rᵇ | Phys. Data |
|---|---|---|---|---|---|
| 636) | H | Br | 3-trifluoromethylphenyl | 4-fluorophenyl | |
| 637) | H | Br | 3-trifluoromethylphenyl | 2,4-difluorophenyl | |
| 638) | H | Br | 3-trifluoromethylphenyl | 4-chlorophenyl | |
| 639) | H | Br | 3-trifluoromethylphenyl | 3-chlorophenyl | |
| 640) | H | Br | 3-trifluoromethylphenyl | 2-chlorophenyl | |
| 641) | H | Br | 3-trifluoromethylphenyl | 4-chloro-2-methoxyphenyl | |
| 642) | H | Br | 3-trifluoromethylphenyl | 4-trifluoromethylphenyl | |
| 643) | H | Br | 3-trifluoromethylphenyl | 2-trifluoromethylphenyl | |
| 644) | H | Br | 3-trifluoromethylphenyl | 3-trifluoromethylphenyl | |
| 645) | H | Br | 3-trifluoromethylphenyl | 4-(trifluoromethoxy)phenyl | |
| 646) | H | Br | 3-trifluoromethylphenyl | 3-(trifluoromethoxy)phenyl | |
| 647) | H | Br | 3-trifluoromethylphenyl | 4-(difluoromethoxy)phenyl | |
| 648) | H | Br | 3-trifluoromethylphenyl | 3-(difluoromethoxy)phenyl | |
| 649) | H | Br | 3-trifluoromethylphenyl | 4-cyanophenyl | |
| 650) | methyl | Br | phenyl | phenyl | |
| 651) | methyl | Br | phenyl | 4-methylphenyl | |
| 652) | methyl | Br | phenyl | 2,4-dichlorophenyl | |
| 653) | methyl | Br | 4-methylphenyl | 4-chlorophenyl | |
| 654) | methyl | Br | 4-methoxyphenyl | 4-methoxyphenyl | |
| 655) | methyl | Br | 4-methoxyphenyl | 2-methoxyphenyl | |
| 656) | methyl | Br | 4-methoxyphenyl | 4-chlorophenyl | |
| 657) | methyl | Br | 4-methoxyphenyl | 2,4-dichlorophenyl | |
| 658) | methyl | Br | 3-chlorophenyl | phenyl | |
| 659) | methyl | Br | 3,4-dichlorophenyl | phenyl | |
| 660) | methyl | Br | 4-chlorophenyl | 4-chlorophenyl | |
| 661) | methyl | Br | 4-chlorophenyl | 3,4-dichlorophenyl | |
| 662) | methyl | Br | 4-chlorophenyl | 2,4-dichlorophenyl | |
| 663) | methyl | Br | 4-chlorophenyl | 4-fluorophenyl | |
| 664) | methyl | Br | 4-chlorophenyl | 4-methylphenyl | |
| 665) | methyl | Br | 4-bromophenyl | 4-methoxyphenyl | |
| 666) | methyl | Br | 4-bromophenyl | 4-methylphenyl | |
| 667) | methyl | Br | phenyl | 4-isopropylphenyl | |
| 668) | methyl | Br | phenyl | 4-fluorophenyl | |
| 669) | methyl | Br | phenyl | 3-fluorophenyl | |
| 670) | methyl | Br | phenyl | 2-fluorophenyl | |
| 671) | methyl | Br | phenyl | 2,3,5,6-tetra-fluorophenyl | |
| 672) | methyl | Br | phenyl | 4-trifluoromethylphenyl | |
| 673) | methyl | Br | phenyl | 3-trifluoromethylphenyl | |
| 674) | methyl | Br | phenyl | 4-methylsulfophenylphenyl | |
| 675) | methyl | Br | phenyl | 4-chlorophenyl | |
| 676) | methyl | Br | phenyl | 3-chlorophenyl | |
| 677) | methyl | Br | phenyl | 2-chlorophenyl | |
| 678) | methyl | Br | phenyl | 3,5-dichlorophenyl | |
| 679) | methyl | Br | phenyl | 4-(trifluoromethoxy)phenyl | |
| 680) | methyl | Br | phenyl | 3-(trifluoromethoxy)phenyl | |
| 681) | methyl | Br | phenyl | 4-(difluoromethoxy)phenyl | |
| 682) | methyl | Br | phenyl | 3-(difluoromethoxy)phenyl | |
| 683) | methyl | Br | phenyl | 4-cyanophenyl | |
| 684) | methyl | Br | 4-chlorophenyl | 4-trifluoromethylphenyl | |
| 685) | methyl | Br | 4-chlorophenyl | 3-trifluoromethylphenyl | |
| 686) | methyl | Br | 4-chlorophenyl | 2-chlorophenyl | |
| 687) | methyl | Br | 4-chlorophenyl | 3-chlorophenyl | |
| 688) | methyl | Br | 4-chlorophenyl | 4-trifluoromethoxyphenyl | |
| 689) | methyl | Br | 4-chlorophenyl | 3-trifluoromethoxyphenyl | |
| 690) | methyl | Br | 4-chlorophenyl | 4-difluoromethoxyphenyl | |
| 691) | methyl | Br | 4-chlorophenyl | 3-difluoromethoxyphenyl | |
| 692) | methyl | Br | 4-fluorophenyl | phenyl | |
| 693) | methyl | Br | 4-fluorophenyl | 4-ethylphenyl | |
| 694) | methyl | Br | 4-fluorophenyl | 4-methylphenyl | |
| 695) | methyl | Br | 4-fluorophenyl | 2-methylphenyl | |
| 696) | methyl | Br | 4-fluorophenyl | 3-methylphenyl | |
| 697) | methyl | Br | 4-fluorophenyl | 4-fluorophenyl | |
| 698) | methyl | Br | 4-fluorophenyl | 2,4-difluorophenyl | |
| 699) | methyl | Br | 4-fluorophenyl | 4-chlorophenyl | |
| 700) | methyl | Br | 4-fluorophenyl | 3-chlorophenyl | |
| 701) | methyl | Br | 4-fluorophenyl | 2-chlorophenyl | |
| 702) | methyl | Br | 4-fluorophenyl | 4-chloro-2-methoxyphenyl | |

TABLE 1-continued

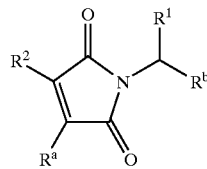

II

| No. | R¹ | R² | Rᵃ | Rᵇ | Phys. Data |
|---|---|---|---|---|---|
| 703) | methyl | Br | 4-fluorophenyl | 4-trifluoromethylphenyl | |
| 704) | methyl | Br | 4-fluorophenyl | 2-trifluoromethylphenyl | |
| 705) | methyl | Br | 4-fluorophenyl | 3-trifluoromethylphenyl | |
| 706) | methyl | Br | 4-fluorophenyl | 4-(trifluoromethoxy)phenyl | |
| 707) | methyl | Br | 4-fluorophenyl | 3-(trifluoromethoxy)phenyl | |
| 708) | methyl | Br | 4-fluorophenyl | 4-(difluoromethoxy)phenyl | |
| 709) | methyl | Br | 4-fluorophenyl | 3-(difluoromethoxy)phenyl | |
| 710) | methyl | Br | 4-fluorophenyl | 4-cyanophenyl | |
| 711) | methyl | Br | 3-fluorophenyl | phenyl | |
| 712) | methyl | Br | 3-fluorophenyl | 4-ethylphenyl | |
| 713) | methyl | Br | 3-fluorophenyl | 4-methylphenyl | |
| 714) | methyl | Br | 3-fluorophenyl | 2-methylphenyl | |
| 715) | methyl | Br | 3-fluorophenyl | 3-methylphenyl | |
| 716) | methyl | Br | 3-fluorophenyl | 4-fluorophenyl | |
| 717) | methyl | Br | 3-fluorophenyl | 2,4-difluorophenyl | |
| 718) | methyl | Br | 3-fluorophenyl | 4-chlorophenyl | |
| 719) | methyl | Br | 3-fluorophenyl | 3-chlorophenyl | |
| 720) | methyl | Br | 3-fluorophenyl | 2-chlorophenyl | |
| 721) | methyl | Br | 3-fluorophenyl | 4-chloro-2-methoxyphenyl | |
| 722) | methyl | Br | 3-fluorophenyl | 4-trifluoromethylphenyl | |
| 723) | methyl | Br | 3-fluorophenyl | 2-trifluoromethylphenyl | |
| 724) | methyl | Br | 3-fluorophenyl | 3-trifluoromethylphenyl | |
| 725) | methyl | Br | 3-fluorophenyl | 4-(trifluoromethoxy)phenyl | |
| 726) | methyl | Br | 3-fluorophenyl | 3-(trifluoromethoxy)phenyl | |
| 727) | methyl | Br | 3-fluorophenyl | 4-(difluoromethoxy)phenyl | |
| 728) | methyl | Br | 3-fluorophenyl | 3-(difluoromethoxy)phenyl | |
| 729) | methyl | Br | 3-fluorophenyl | 4-cyanophenyl | |
| 730) | methyl | Br | 2-fluorophenyl | phenyl | |
| 731) | methyl | Br | 2-fluorophenyl | 4-ethylphenyl | |
| 732) | methyl | Br | 2-fluorophenyl | 4-methylpnenyl | |
| 733) | methyl | Br | 2-fluorophenyl | 2-methylphenyl | |
| 734) | methyl | Br | 2-fluorophenyl | 3-methylphenyl | |
| 735) | methyl | Br | 2-fluorophenyl | 4-fluorophenyl | |
| 736) | methyl | Br | 2-fluorophenyl | 2,4-difluorophenyl | |
| 737) | methyl | Br | 2-fluorophenyl | 4-chlorophenyl | |
| 738) | methyl | Br | 2-fluorophenyl | 3-chlorophenyl | |
| 739) | methyl | Br | 2-fluorophenyl | 2-chlorophenyl | |
| 740) | methyl | Br | 2-fluorophenyl | 4-chloro-2-methoxyphenyl | |
| 741) | methyl | Br | 2-fluorophenyl | 4-trifluoromethylphenyl | |
| 742) | methyl | Br | 2-fluorophenyl | 2-trifluoromethylphenyl | |
| 743) | methyl | Br | 2-fluorophenyl | 3-trifluoromethylphenyl | |
| 744) | methyl | Br | 2-fluorophenyl | 4-(trifluoromethoxy)phenyl | |
| 745) | methyl | Br | 2-fluorophenyl | 3-(trifluoromethoxy)phenyl | |
| 746) | methyl | Br | 2-fluorophenyl | 4-(difluoromethoxy)phenyl | |
| 747) | methyl | Br | 2-fluorophenyl | 3-(difluoromethoxy)phenyl | |
| 748) | methyl | Br | 2-fluorophenyl | 4-cyanophenyl | |
| 749) | methyl | Br | 2,4-difluorophenyl | phenyl | |
| 750) | methyl | Br | 2,4-difluorophenyl | 4-ethylphenyl | |
| 751) | methyl | Br | 2,4-difluorophenyl | 4-methylphenyl | |
| 752) | methyl | Br | 2,4-difluorophenyl | 2-methylphenyl | |
| 753) | methyl | Br | 2,4-difluorophenyl | 3-methylphenyl | |
| 754) | methyl | Br | 2,4-difluorophenyl | 4-fluorophenyl | |
| 755) | methyl | Br | 2,4-difluorophenyl | 2,4-difluorophenyl | |
| 756) | methyl | Br | 2,4-difluorophenyl | 4-chlorophenyl | |
| 757) | methyl | Br | 2,4-difluorophenyl | 3-chlorophenyl | |
| 758) | methyl | Br | 2,4-difluorophenyl | 2-chlorophenyl | |
| 759) | methyl | Br | 2,4-difluorophenyl | 4-chloro-2-methoxyphenyl | |
| 760) | methyl | Br | 2,4-difluorophenyl | 4-trifluoromethylphenyl | |
| 761) | methyl | Br | 2,4-difluorophenyl | 2-trifluoromethylphenyl | |
| 762) | methyl | Br | 2,4-difluorophenyl | 3-trifluoromethylphenyl | |
| 763) | methyl | Br | 2,4-difluorophenyl | 4-(trifluoromethoxy)phenyl | |
| 764) | methyl | Br | 2,4-difluorophenyl | 3-(trifluoromethoxy)phenyl | |
| 765) | methyl | Br | 2,4-difluorophenyl | 4-(difluoromethoxy)phenyl | |
| 766) | methyl | Br | 2,4-difluorophenyl | 3-(difluoromethoxy)phenyl | |
| 767) | methyl | Br | 2,4-difluorophenyl | 4-cyanophenyl | |
| 768) | methyl | Br | 4-trifluoromethylphenyl | phenyl | |
| 769) | methyl | Br | 4-trifluoromethylphenyl | 4-ethylphenyl | |

TABLE 1-continued

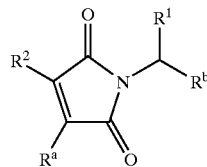

II

| No. | R¹ | R² | Rᵃ | Rᵇ | Phys. Data |
|---|---|---|---|---|---|
| 770) | methyl | Br | 4-trifluoromethylphenyl | 4-methylphenyl | |
| 771) | methyl | Br | 4-trifluoromethylphenyl | 2-methylphenyl | |
| 772) | methyl | Br | 4-trifluoromethylphenyl | 3-methylphenyl | |
| 773) | methyl | Br | 4-trifluoromethylphenyl | 4-fluorophenyl | |
| 774) | methyl | Br | 4-trifluoromethylphenyl | 2,4-difluorophenyl | |
| 775) | methyl | Br | 4-trifluoromethylphenyl | 4-chlorophenyl | |
| 776) | methyl | Br | 4-trifluoromethylphenyl | 3-chlorophenyl | |
| 777) | methyl | Br | 4-trifluoromethylphenyl | 2-chlorophenyl | |
| 778) | methyl | Br | 4-trifluoromethylphenyl | 4-chloro-2-methoxyphenyl | |
| 779) | methyl | Br | 4-trifluoromethylphenyl | 4-trifluoromethylphenyl | |
| 780) | methyl | Br | 4-trifluoromethylphenyl | 2-trifluoromethylphenyl | |
| 781) | methyl | Br | 4-trifluoromethylphenyl | 3-trifluoromethylphenyl | |
| 782) | methyl | Br | 4-trifluoromethylphenyl | 4-(trifluoromethoxy)phenyl | |
| 783) | methyl | Br | 4-trifluoromethylphenyl | 3-(trifluoromethoxy)phenyl | |
| 784) | methyl | Br | 4-trifluoromethylphenyl | 4-(difluoromethoxy)phenyl | |
| 785) | methyl | Br | 4-trifluoromethylphenyl | 3-(difluoromethoxy)phenyl | |
| 786) | methyl | Br | 4-trifluoromethylphenyl | 4-cyanophenyl | |
| 787) | methyl | Br | 3,4-dichloromethylphenyl | 4-fluorophenyl | |
| 788) | methyl | Br | 3,4-(methylenedioxy)phenyl | phenyl | |
| 789) | methyl | Br | 3-trifluoromethylphenyl | phenyl | |
| 790) | methyl | Br | 3-trifluoromethylphenyl | 4-ethylphenyl | |
| 791) | methyl | Br | 3-trifluoromethylphenyl | 4-methylphenyl | |
| 792) | methyl | Br | 3-trifluoromethylphenyl | 2-methylphenyl | |
| 793) | methyl | Br | 3-trifluoromethylphenyl | 3-methylphenyl | |
| 794) | methyl | Br | 3-trifluoromethylphenyl | 4-fluorophenyl | |
| 795) | methyl | Br | 3-trifluoromethylphenyl | 2,4-difluorophenyl | |
| 796) | methyl | Br | 3-trifluoromethylphenyl | 4-chlorophenyl | |
| 797) | methyl | Br | 3-trifluoromethylphenyl | 3-chlorophenyl | |
| 798) | methyl | Br | 3-trifluoromethylphenyl | 2-chlorophenyl | |
| 799) | methyl | Br | 3-trifluoromethylphenyl | 4-chloro-2-methoxyphenyl | |
| 800) | methyl | Br | 3-trifluoromethylphenyl | 4-trifluoromethylphenyl | |
| 801) | methyl | Br | 3-trifluoromethylphenyl | 2-trifluoromethylphenyl | |
| 802) | methyl | Br | 3-trifluoromethylphenyl | 3-trifluoromethylphenyl | |
| 803) | methyl | Br | 3-trifluoromethylphenyl | 4-(trifluoromethoxy)phenyl | |
| 804) | methyl | Br | 3-trifluoromethylphenyl | 3-(trifluoromethoxy)phenyl | |
| 805) | methyl | Br | 3-trifluoromethylphenyl | 4-(difluoromethoxy)phenyl | |
| 806) | methyl | Br | 3-trifluoromethylphenyl | 3-(difluoromethoxy)phenyl | |
| 807) | methyl | Br | 3-trifluoromethylphenyl | 4-cyanophenyl | |
| 808) | formyl | Br | phenyl | phenyl | |
| 809) | formyl | Br | phenyl | 4-methylphenyl | |
| 810) | formyl | Br | phenyl | 2,4-dichlorophenyl | |
| 811) | formyl | Br | 4-methylphenyl | 4-chlorophenyl | |
| 812) | formyl | Br | 4-methoxyphenyl | 4-methoxyphenyl | |
| 813) | formyl | Br | 4-methoxyphenyl | 2-methoxyphenyl | |
| 814) | formyl | Br | 4-methoxyphenyl | 4-chlorophenyl | |
| 815) | formyl | Br | 4-methoxyphenyl | 2,4-dichlorophenyl | |
| 816) | formyl | Br | 3-chlorophenyl | phenyl | |
| 817) | formyl | Br | 3,4-dichlorophenyl | phenyl | |
| 818) | formyl | Br | 4-chlorophenyl | 4-chlorophenyl | |
| 819) | formyl | Br | 4-chlorophenyl | 3,4-dichlorophenyl | |
| 820) | formyl | Br | 4-chlorophenyl | 2,4-dichlorophenyl | |
| 821) | formyl | Br | 4-chlorophenyl | 4-fluorophenyl | |
| 822) | formyl | Br | 4-chlorophenyl | 4-formylphenyl | |
| 823) | formyl | Br | 4-bromophenyl | 4-methoxyphenyl | |
| 824) | formyl | Br | 4-bromophenyl | 4-formylphenyl | |
| 825) | formyl | Br | phenyl | 4-isopropylphenyl | |
| 826) | formyl | Br | phenyl | 4-fluorophenyl | |
| 827) | formyl | Br | phenyl | 3-fluorophenyl | |
| 828) | formyl | Br | phenyl | 2-fluorophenyl | |
| 829) | formyl | Br | phenyl | 2,3,5,6-tetra-fluorophenyl | |
| 830) | formyl | Br | phenyl | 4-trifluoromethylphenyl | |
| 831) | formyl | Br | phenyl | 3-trifluoromethylphenyl | |
| 832) | formyl | Br | phenyl | 4-formylsulfonylphenyl | |
| 833) | formyl | Br | phenyl | 4-chlorophenyl | |
| 834) | formyl | Br | phenyl | 3-chlorophenyl | |
| 835) | formyl | Br | phenyl | 2-chlorophenyl | |
| 836) | formyl | Br | phenyl | 3,5-dichlorophenyl | |

TABLE 1-continued

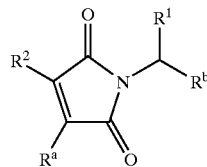

II

| No. | R¹ | R² | Rᵃ | Rᵇ | Phys. Data |
|---|---|---|---|---|---|
| 837) | formyl | Br | phenyl | 4-(trifluoromethoxy)phenyl | |
| 838) | formyl | Br | phenyl | 3-(trifluoromethoxy)phenyl | |
| 839) | formyl | Br | phenyl | 4-(difluoromethoxy)phenyl | |
| 840) | formyl | Br | phenyl | 3-(difluoromethoxy)phenyl | |
| 841) | formyl | Br | phenyl | 4-cyanophenyl | |
| 842) | formyl | Br | 4-chlorophenyl | 4-trifluoroethylphenyl | |
| 843) | formyl | Br | 4-chlorophenyl | 3-trifluoromethylphenyl | |
| 844) | formyl | Br | 4-chlorophenyl | 2-chlorophenyl | |
| 845) | formyl | Br | 4-chlorophenyl | 3-chlorophenyl | |
| 846) | formyl | Br | 4-chlorophenyl | 4-trifluoromethoxyphenyl | |
| 847) | formyl | Br | 4-chlorophenyl | 3-trifluoromethoxyphenyl | |
| 848) | formyl | Br | 4-chlorophenyl | 4-difluoromethoxyphenyl | |
| 849) | formyl | Br | 4-chlorophenyl | 3-difluoromethoxyphenyl | |
| 850) | formyl | Br | 4-fluorophenyl | phenyl | |
| 851) | formyl | Br | 4-fluorophenyl | 4-ethylphenyl | |
| 852) | formyl | Br | 4-fluorophenyl | 4-formylphenyl | |
| 853) | formyl | Br | 4-fluorophenyl | 2-formylphenyl | |
| 854) | formyl | Br | 4-fluorophenyl | 3-formylphenyl | |
| 855) | formyl | Br | 4-fluorophenyl | 4-fluorophenyl | |
| 856) | formyl | Br | 4-fluorophenyl | 2,4-difluorophenyl | |
| 857) | formyl | Br | 4-fluorophenyl | 4-chlorophenyl | |
| 858) | formyl | Br | 4-fluorophenyl | 3-chlorophenyl | |
| 859) | formyl | Br | 4-fluorophenyl | 2-chlorophenyl | |
| 860) | formyl | Br | 4-fluorophenyl | 4-chloro-2-methoxyphenyl | |
| 861) | formyl | Br | 4-fluorophenyl | 4-trifluoromethylphenyl | |
| 862) | formyl | Br | 4-fluorophenyl | 2-trifluoromethylphenyl | |
| 863) | formyl | Br | 4-fluorophenyl | 3-trifluoromethylphenyl | |
| 864) | formyl | Br | 4-fluorophenyl | 4-(trifluoromethoxy)phenyl | |
| 865) | formyl | Br | 4-fluorophenyl | 3-(trifluoromethoxy)phenyl | |
| 866) | formyl | Br | 4-fluorophenyl | 4-(difluoromethoxy)phenyl | |
| 867) | formyl | Br | 4-fluorophenyl | 3-(difluoromethoxy)phenyl | |
| 868) | formyl | Br | 4-fluorophenyl | 4-cyanophenyl | |
| 869) | formyl | Br | 3-fluorophenyl | phenyl | |
| 870) | formyl | Br | 3-fluorophenyl | 4-ethylphenyl | |
| 871) | formyl | Br | 3-fluorophenyl | 4-formylphenyl | |
| 872) | formyl | Br | 3-fluorophenyl | 2-formylphenyl | |
| 873) | formyl | Br | 3-fluorophenyl | 3-formylphenyl | |
| 874) | formyl | Br | 3-fluorophenyl | 4-fluorophenyl | |
| 875) | formyl | Br | 3-fluorophenyl | 2,4-difluorophenyl | |
| 876) | formyl | Br | 3-fluorophenyl | 4-chlorophenyl | |
| 877) | formyl | Br | 3-fluorophenyl | 3-chlorophenyl | |
| 878) | formyl | Br | 3-fluorophenyl | 2-chlorophenyl | |
| 879) | formyl | Br | 3-fluorophenyl | 4-chloro-2-methoxyphenyl | |
| 880) | formyl | Br | 3-fluorophenyl | 4-trifluoromethylphenyl | |
| 881) | formyl | Br | 3-fluorophenyl | 2-trifluoromethylphenyl | |
| 882) | formyl | Br | 3-fluorophenyl | 3-trifluoromethylphenyl | |
| 883) | formyl | Br | 3-fluorophenyl | 4-(trifluoromethoxy)phenyl | |
| 884) | formyl | Br | 3-fluorophenyl | 3-(trifluoromethoxy)phenyl | |
| 885) | formyl | Br | 3-fluorophenyl | 4-(difluoromethoxy)phenyl | |
| 886) | formyl | Br | 3-fluorophenyl | 3-(difluoromethoxy)phenyl | |
| 887) | formyl | Br | 3-fluorophenyl | 4-cyanophenyl | |
| 888) | formyl | Br | 2-fluorophenyl | phenyl | |
| 889) | formyl | Br | 2-fluorophenyl | 4-ethylphenyl | |
| 890) | formyl | Br | 2-fluorophenyl | 4-formylphenyl | |
| 891) | formyl | Br | 2-fluorophenyl | 2-formylphenyl | |
| 892) | formyl | Br | 2-fluorophenyl | 3-formylphenyl | |
| 893) | formyl | Br | 2-fluorophenyl | 4-fluorophenyl | |
| 894) | formyl | Br | 2-fluorophenyl | 2,4-difluorophenyl | |
| 895) | formyl | Br | 2-fluorophenyl | 4-chlorophenyl | |
| 896) | formyl | Br | 2-fluorophenyl | 3-chlorophenyl | |
| 897) | formyl | Br | 2-fluorophenyl | 2-chlorophenyl | |
| 898) | formyl | Br | 2-fluorophenyl | 4-chloro-2-methoxyphenyl | |
| 899) | formyl | Br | 2-fluorophenyl | 4-trifluoromethylphenyl | |
| 900) | formyl | Br | 2-fluorophenyl | 2-trifluoromethylphenyl | |
| 901) | formyl | Br | 2-fluorophenyl | 3-trifluoromethylphenyl | |
| 902) | formyl | Br | 2-fluorophenyl | 4-(trifluoromethoxy)phenyl | |
| 903) | formyl | Br | 2-fluorophenyl | 3-(trifluoromethoxy)phenyl | |

TABLE 1-continued

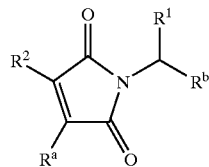

II

| No. | R¹ | R² | Rᵃ | Rᵇ | Phys. Data |
|---|---|---|---|---|---|
| 904) | formyl | Br | 2-fluorophenyl | 4-(difluoromethoxy)phenyl | |
| 905) | formyl | Br | 2-fluorophenyl | 3-(difluoromethoxy)phenyl | |
| 906) | formyl | Br | 2-fluorophenyl | 4-cyanophenyl | |
| 907) | formyl | Br | 2,4-difluorophenyl | phenyl | |
| 908) | formyl | Br | 2,4-difluorophenyl | 4-ethylphenyl | |
| 909) | formyl | Br | 2,4-difluorophenyl | 4-formylphenyl | |
| 910) | formyl | Br | 2,4-difluorophenyl | 2-formylphenyl | |
| 911) | formyl | Br | 2,4-difluorophenyl | 3-formylphenyl | |
| 912) | formyl | Br | 2,4-difluorophenyl | 4-fluorophenyl | |
| 913) | formyl | Br | 2,4-difluorophenyl | 2,4-difluorophenyl | |
| 914) | formyl | Br | 2,4-difluorophenyl | 4-chlorophenyl | |
| 915) | formyl | Br | 2,4-difluorophenyl | 3-chlorophenyl | |
| 916) | formyl | Br | 2,4-difluorophenyl | 2-chlorophenyl | |
| 917) | formyl | Br | 2,4-difluorophenyl | 4-chloro-2-methoxyphenyl | |
| 918) | formyl | Br | 2,4-difluorophenyl | 4-trifluoromethylphenyl | |
| 919) | formyl | Br | 2,4-difluorophenyl | 2-trifluoromethylphenyl | |
| 920) | formyl | Br | 2,4-difluorophenyl | 3-trifluoromethylphenyl | |
| 921) | formyl | Br | 2,4-difluorophenyl | 4-(trifluoromethoxy)phenyl | |
| 922) | formyl | Br | 2,4-difluorophenyl | 3-(trifluoromethoxy)phenyl | |
| 923) | formyl | Br | 2,4-difluorophenyl | 4-(difluoromethoxy)phenyl | |
| 924) | formyl | Br | 2,4-difluorophenyl | 3-(difluoromethoxy)phenyl | |
| 925) | formyl | Br | 2,4-difluorophenyl | 4-cyanophenyl | |
| 926) | formyl | Br | 4-trifluoromethylphenyl | phenyl | |
| 927) | formyl | Br | 4-trifluoromethylphenyl | 4-ethylphenyl | |
| 928) | formyl | Br | 4-trifluoromethylphenyl | 4-formylphenyl | |
| 929) | formyl | Br | 4-trifluoromethylphenyl | 2-formylphenyl | |
| 930) | formyl | Br | 4-trifluoromethylphenyl | 3-formylphenyl | |
| 931) | formyl | Br | 4-trifluoromethylphenyl | 4-fluorophenyl | |
| 932) | formyl | Br | 4-trifluoromethylphenyl | 2,4-difluorophenyl | |
| 933) | formyl | Br | 4-trifluoromethylphenyl | 4-chlorophenyl | |
| 934) | formyl | Br | 4-trifluoromethylphenyl | 3-chlorophenyl | |
| 935) | formyl | Br | 4-trifluoromethylphenyl | 2-chlorophenyl | |
| 936) | formyl | Br | 4-trifluoromethylphenyl | 4-chloro-2-methoxyphenyl | |
| 937) | formyl | Br | 4-trifluoromethylphenyl | 4-trifluoromethylphenyl | |
| 938) | formyl | Br | 4-trifluoromethylphenyl | 2-trifluoromethylphenyl | |
| 939) | formyl | Br | 4-trifluoromethylphenyl | 3-trifluoromethylphenyl | |
| 940) | formyl | Br | 4-trifluoromethylphenyl | 4-(trifluoromethoxy)phenyl | |
| 941) | formyl | Br | 4-trifluoromethylphenyl | 3-(trifluoromethoxy)phenyl | |
| 942) | formyl | Br | 4-trifluoromethylphenyl | 4-(difluoromethoxy)phenyl | |
| 943) | formyl | Br | 4-trifluoromethylphenyl | 3-(difluoromethoxy)phenyl | |
| 944) | formyl | Br | 4-trifluoromethylphenyl | 4-cyanophenyl | |
| 945) | formyl | Br | 3,4-dichloromethylphenyl | 4-fluorophenyl | |
| 946) | formyl | Br | 3,4-(formylenedioxy)phenyl | phenyl | |
| 947) | formyl | Br | 3-trifluoromethylphenyl | phenyl | |
| 948) | formyl | Br | 3-trifluoromethylphenyl | 4-ethylphenyl | |
| 949) | formyl | Br | 3-trifluoromethylphenyl | 4-formylphenyl | |
| 950) | formyl | Br | 3-trifluoromethylphenyl | 2-formylphenyl | |
| 951) | formyl | Br | 3-trifluoromethylphenyl | 3-formylphenyl | |
| 952) | formyl | Br | 3-trifluoromethylphenyl | 4-fluorophenyl | |
| 953) | formyl | Br | 3-trifluoromethylphenyl | 2,4-difluorophenyl | |
| 954) | formyl | Br | 3-trifluoromethylphenyl | 4-chlorophenyl | |
| 955) | formyl | Br | 3-trifluoromethylphenyl | 3-chlorophenyl | |
| 956) | formyl | Br | 3-trifluoromethylphenyl | 2-chlorophenyl | |
| 957) | formyl | Br | 3-trifluoromethylphenyl | 4-chloro-2-methoxyphenyl | |
| 958) | formyl | Br | 3-trifluoromethylphenyl | 4-trifluoromethylphenyl | |
| 959) | formyl | Br | 3-trifluoromethylphenyl | 2-trifluoromethylphenyl | |
| 960) | formyl | Br | 3-trifluoromethylphenyl | 3-trifluoromethylphenyl | |
| 961) | formyl | Br | 3-trifluoromethylphenyl | 4-(trifluoromethoxy)phenyl | |
| 962) | formyl | Br | 3-trifluoromethylphenyl | 3-(trifluoromethoxy)phenyl | |
| 963) | formyl | Br | 3-trifluoromethylphenyl | 4-(difluoromethoxy)phenyl | |
| 964) | formyl | Br | 3-trifluoromethylphenyl | 3-(difluoromethoxy)phenyl | |
| 965) | formyl | Br | 3-trifluoromethylphenyl | 4-cyanophenyl | |
| 966) | formyl | Br | 4-formylphenyl | phenyl | |
| 967) | formyl | Br | 4-methoxyphenyl | phenyl | |
| 968) | formyl | Br | 4-chlorophenyl | phenyl | |
| 969) | H | Cl | 2-chloro-6-fluorophenyl | phenyl | |
| 970) | H | Cl | 2-chloro-6-fluorophenyl | 4-fluorophenyl | |

TABLE 1-continued

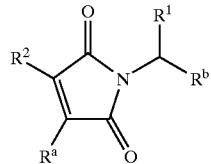

II

| No. | $R^1$ | $R^2$ | $R^a$ | $R^b$ | Phys. Data |
|---|---|---|---|---|---|
| 971) | H | Cl | phenyl | 4-cyanophenyl | |
| 972) | H | Cl | phenyl | 4-bromophenyl | |
| 973) | H | Cl | phenyl | 4-iodophenyl | |
| 974) | acetyl | Cl | phenyl | phenyl | |
| 975) | formyl | Cl | phenyl | phenyl | |
| 976) | H | Cl | 4-phenylphenyl | 4-fluorophenyl | |
| 977) | H | Cl | 2,6-dichlorophenyl | phenyl | |
| 978) | H | Cl | 4-phenylphenyl | phenyl | |
| 979) | methyl | Cl | 4-phenylphenyl | phenyl | |
| 980) | acetyl | Cl | 4-chlorophenyl | phenyl | m.p. 138–140° C. |
| 981) | | | | | |
| 982) | H | OMe | 2-chloro-6-fluorophenyl | phenyl | |
| 983) | H | OMe | 2-chloro-6-fluorophenyl | 4-fluorophenyl | |
| 984) | H | OMe | phenyl | 4-cyanophenyl | |
| 985) | H | OMe | phenyl | 4-bromophenyl | |
| 986) | H | OMe | phenyl | 4-iodophenyl | |
| 987) | acetyl | OMe | phenyl | phenyl | |
| 988) | formyl | OMe | phenyl | phenyl | |
| 989) | H | OMe | 4-phenylphenyl | 4-fluorophenyl | |
| 990) | H | OMe | 2,6-dichlorophenyl | phenyl | |
| 991) | H | OMe | 4-phenylphenyl | phenyl | |
| 992) | methyl | OMe | 4-phenylphenyl | phenyl | |
| 993) | acetyl | OMe | 4-chlorophenyl | phenyl | |
| 994) | formyl | OMe | 4-chlorophenyl | phenyl | |
| 995) | methyl | OMe | phenyl | phenyl | |
| 996) | H | OMe | 3,4-dichlorophenyl | 4-fluorophenyl | |
| 997) | H | OMe | 3,4-(methylenedioxy)phenyl | phenyl | |
| 998) | H | OMe | 4-fluorophenyl | phenyl | |
| 999) | H | OMe | 4-fluorophenyl | 4-fluorophenyl | |
| 1000) | H | OMe | 4-chlorophenyl | 2-chlorophenyl | |
| 1001) | H | OMe | 4-chlorophenyl | 3-chlorophenyl | |
| 1002) | H | OMe | 4-chlorophenyl | 4-trifluoromethylphenyl | |
| 1003) | H | OMe | phenyl | 3,5-dichlorophenyl | |
| 1004) | H | OMe | phenyl | 4-(trifluoromethoxy)phenyl | |
| 1005) | H | OMe | phenyl | phenyl | |
| 1006) | H | OMe | phenyl | 4-methylphenyl | |
| 1007) | H | OMe | phenyl | 2,4-dichlorophenyl | |
| 1008) | H | OMe | 4-methylphenyl | phenyl | |
| 1009) | H | OMe | 4-methylphenyl | 4-chlorophenyl | |
| 1010) | H | OMe | 4-methoxyphenyl | phenyl | |
| 1011) | H | OMe | 4-methoxyphenyl | 4-methoxyphenyl | |
| 1012) | H | OMe | 4-methoxyphenyl | 2-methoxyphenyl | |
| 1013) | H | OMe | 4-methoxyphenyl | 4-chlorophenyl | |
| 1014) | H | OMe | 4-methoxyphenyl | 2,4-dichlorophenyl | |
| 1015) | H | OMe | 3-chlorophenyl | phenyl | |
| 1016) | H | OMe | 3,4-dichlorophenyl | phenyl | |
| 1017) | H | OMe | 4-chlorophenyl | phenyl | |
| 1018) | H | OMe | 4-chlorophenyl | 4-chlorophenyl | |
| 1019) | H | OMe | 4-chlorophenyl | 3,4-dichlorophenyl | |
| 1020) | H | OMe | 4-chlorophenyl | 2,4-dichlorophenyl | |
| 1021) | H | OMe | 4-chlorophenyl | 4-fluorophenyl | |
| 1022) | H | OMe | 4-chlorophenyl | 4-methylphenyl | |
| 1023) | H | OMe | 4-bromophenyl | 4-methoxyphenyl | |
| 1024) | H | OMe | 4-bromophenyl | 4-methylphenyl | |
| 1025) | methyl | OMe | 4-methylphenyl | phenyl | |
| 1026) | methyl | OMe | 4-methoxyphenyl | phenyl | |
| 1027) | methyl | OMe | 4-chlorophenyl | phenyl | |
| 1028) | acetyl | OMe | phenyl | phenyl | |
| 1029) | trifluoro-acetyl | OMe | phenyl | phenyl | |
| 1030) | H | OMe | phenyl | 4-isopropylphenyl | |
| 1031) | H | OMe | phenyl | 4-fluorophenyl | |
| 1032) | H | OMe | phenyl | 3-fluorophenyl | |
| 1033) | H | OMe | phenyl | 2-fluorophenyl | |
| 1034) | H | OMe | phenyl | 2,3,5,6-tetra-fluorophenyl | |
| 1035) | H | OMe | phenyl | 4-trifluoromethylphenyl | |
| 1036) | H | OMe | phenyl | 3-trifluoromethylphenyl | |

TABLE 1-continued

Structure II

| No. | R¹ | R² | Rᵃ | Rᵇ | Phys. Data |
|---|---|---|---|---|---|
| 1037) | H | OMe | phenyl | 4-methylsulfophenylphenyl | |
| 1038) | H | OMe | phenyl | 4-chlorophenyl | |
| 1039) | H | OMe | phenyl | 3-chlorophenyl | |
| 1040) | H | OMe | phenyl | 2-chlorophenyl | |
| 1041) | H | SMe | phenyl | phenyl | m.p. 86–88° C. |
| 1042) | H | S(O)Me | phenyl | phenyl | m.p. 178–180° C. |
| 1043) | H | SO₂Me | phenyl | phenyl | m.p. 194–196° C. |
| 1044) | H | Cl | 4-bromophenyl | phenyl | m.p. 147–149° C. |
| 1045) | H | Br | 4-bromophenyl | phenyl | |
| 1046) | H | Cl | 4-phenylphenyl | phenyl | m.p. 177–179° C. |
| 1047) | H | NMe₂ | phenyl | phenyl | |
| 1048) | H | NMe₂ | phenyl | 4-fluorophenyl | |
| 1049) | H | NMe₂ | 4-chlorophenyl | phenyl | |
| 1050) | H | NEt₂ | phenyl | phenyl | |
| 1051) | H | NEt₂ | 4-chlorophenyl | phenyl | |
| 1052) | H | NEt₂ | phenyl | 4-fluorophenyl | |
| 1053) | H | NHMe | phenyl | phenyl | |
| 1054) | H | CHF₂O | phenyl | phenyl | |
| 1055) | H | CHF₂O | 4-chlorophenyl | phenyl | |
| 1056) | H | CHF₂O | phenyl | 4-fluorophenyl | |
| 1057) | H | MeOCH₂ | phenyl | phenyl | |
| 1058) | H | MeOCH₂ | 4-chlorophenyl | phenyl | |
| 1059) | H | MeOCH₂ | phenyl | 4-fluorophenyl | |
| 1060) | formyl | Cl | 4-chlorophenyl | phenyl | m.p. 164–166° C. |

The compounds of the formula I can be prepared, for example, according to the reaction scheme below:

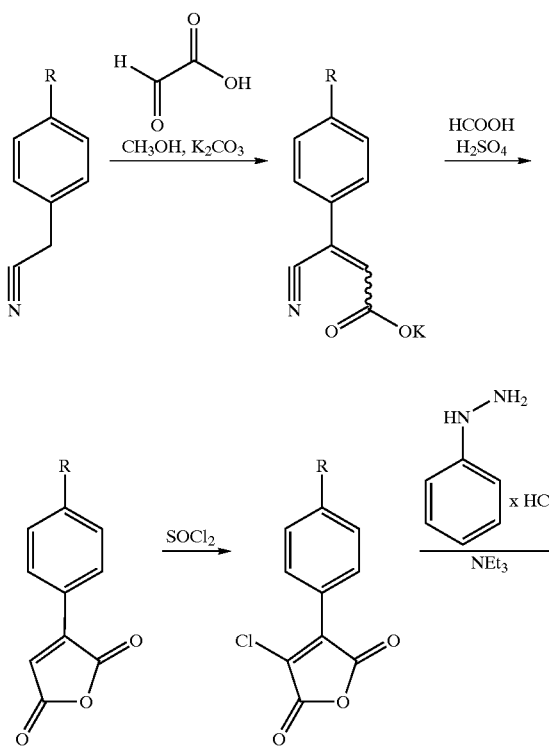

-continued

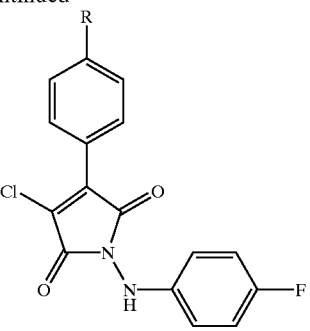

Compounds of the formula II are in particular those in which R¹ is hydrogen or a $C_1$–$C_4$-alkyl group or a formyl group (—CHO). Preference is furthermore given to compounds II in which the radicals R², Rᵃ and Rᵇ independently of one another have the following meanings:

R² is halogen, $C_1$–$C_6$-alkoxy, $C_1$–$C_6$-alkylthio, halo-$C_1$–$C_6$-alkyl, halo-$C_1$–$C_6$-alkoxy;

Rᵃ is phenyl which may be mono- or polysubstituted, preferably mono- or disubstituted, by halogen, halo-$C_1$–$C_6$-alkyl or by a phenyl group which for its part may also be substituted by halogen or $C_1$–$C_4$-alkyl;

Rᵇ is phenyl which may be mono- or polysubstituted, preferably mono- to tetrasubstituted, by halogen, $C_1$–$C_6$-alkyl, $C_1$–$C_4$-haloalkyl, $C_1$–$C_4$-haloalkoxy.

In This context, the radicals R¹, Rᵃ and Rᵇ, in the case of the compounds II, have, for example, the following meanings:

R¹: hydrogen, methyl, formyl, acetyl;
R²: halogen;

$R^a$: phenyl, 4-chlorophenyl, 4-fluorophenyl, 3,4-dichlorophenyl, 2-chloro-6-fluorophenyl, 4-phenylphenyl, 2,6-dichlorophenyl or 2-chlorophenyl;

$R^b$: 4-isopropylphenyl, 2,3,5,6-tetrafluorophenyl, 4-trifluoromethylphenyl, 4-chlorophenyl, 3-chlorophenyl, 2-chlorophenyl, 3,5-dichlorophenyl,
4-(trifluoromethoxy)phenyl, 4-trifluoromethylphenyl, phenyl,
4-fluorophenyl, 4-cyanophenyl, 4-bromophenyl, 4-iodophenyl.

The compounds I have excellent fungicidal activity. This is particularly true for the compounds Nos. 1, 6, 23, 27, 486, 1041, 1042, 1043, 1044, 1045 and 1046 listed in Table 1.

Usually, the plants are sprayed or dusted with the active compounds, or the seeds of the plants are treated with the active compounds.

The formulations (fungicidal compositions or agrochemical compositions) are prepared in a known manner, e.g. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly disperse silica, silicates); emulsifiers such as non-ionic and anionic emulsifiers (e.g. polyoxyethylene fatty alcohol ethers, alkylsulfonates and arylsulfonates) and dispersants such as lignosulfite waste liquors and methylcellulose.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkylsulfonates, alkylarylsulfonates, alkyl sulfates, lauryl ether sulfates and fatty alcohol sulfates, 10 and salts of sulfated hexa-, hepta- and octadecanols, and of fatty alcohol glycol ethers, condensates of sulfonated naphthalene and its derivatives with formaldehyde, condensates of naphthalene or of the naphthalenesulfonic acids with phenol or formaldehyde, polyoxyethylene octylphenol ether, ethoxylated isooctylphenol, octylphenol or nonylphenol, alkylphenol polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, liquosulfite waste liquors and methylcellulose.

Powders, materials for spreading and dusts can be prepared by mixing or concomitantly grinding the active substances with a solid carrier.

Granules, e.g. coated granules, impregnated granules and homogeneous granules, can be prepared by binding the active ingredients to solid carriers. Examples of solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders or other solid carriers.

The following are examples of such formulations:

I. a solution, suitable for use in the form of microdrops, of 90 parts by weight of a compound I according to the invention and 10 parts by weight of N-methyl-2-pyrrolidone;

II. a mixture of 10 parts by weight of a compound I according to the invention, 70 parts by weight of xylene, 10 parts by weight of the adduct of 8 to 10 mol of ethylene oxide and 1 mol of oleic acid N-monoethanolamide, 5 parts by weight of calcium dodecylbenzenesulfonate, 5 parts by weight of the adduct of 40 mol of ethylene oxide to 1 mol of castor oil; a dispersion is obtained by finely distributing the solution in water.

III. an aqueous dispersion of 10 parts by weight of a compound I according to the invention, 40 parts by weight of cyclohexanone, 30 parts by weight of isobutanol, 20 parts by weight of the adduct of 40 mol of ethylene oxide and 1 mol of castor oil;

IV. an aqueous dispersion of 10 parts by weight of a compound I according to the invention, 25 parts by weight of cyclohexanol, 55 parts by weight of a mineral oil fraction of boiling point 210 to 280° C. and 10 parts by weight of the adduct of 40 mol of ethylene oxide and 1 mol of castor oil;

V. a mixture, ground in a hammer mill, of 80 parts by weight, preferably of a solid compound I according to the invention, 3 parts by weight of sodium di-iso-butylnaphthalene-2-sulfonate, 10 parts by weight of the sodium salt of a lignosulfonic acid from a sulfite waste liquor and 7 parts by weight of pulverulent silica gel; a spray mixture is obtained by finely distributing the mixture in water;

VI. an intimate mixture of 3 parts by weight of a compound I according to the invention and 97 parts by weight of finely divided kaolin; this dust comprises 3% by weight of active ingredient;

VII. an intimate mixture of 30 parts by weight of a compound I according to the invention, 62 parts by weight of pulverulent silica gel and 8 parts by weight of paraffin oil which had been sprayed onto the surface of this silica gel; this formulation imparts good adhesion to the active ingredient;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water; this dispersion can be diluted further;

IX. a stable oily dispersion of 20 parts by weight of a compound I according to the invention, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 50 parts by weight of a paraffinic mineral oil.

The active compounds of the formula I have excellent activity against a broad spectrum of phytopathogenic fungi, in particular from the classes of the Ascomycetes, Deuteromycetes, Phycomycetes and Basidiomycetes. Some of them act systemically, and they can therefore also be employed as foliar and soil-acting fungicides.

They are especially important for controlling a large number of fungi on a variety of crop plants such as wheat, rye, barley, oats, rice, maize, turf, cotton, soya, coffee, sugar cane, grapevines, fruit species, ornamentals and vegetables such as cucumbers, beans and cucurbits, and on the seeds of these plants.

The compounds are applied by treating the fungi, or the seeds, plants, materials or the soil to be protected against fungal infection, with a fungicidally active amount of the active ingredients. Application can be effected both before and after infection of the materials, plants or seeds by the fungi.

Specifically, the novel compounds are suitable for controlling the following plant diseases: *Erysiphe graminis* (powdery mildew) in cereals, *Erysiphe cichoracearum* and *Sphaerotheca fuliginea* on cucurbits, *Podosphaera leucotricha* on apples, *Uncinula necator* on grapevines, Puccinia species on cereals, Rhizoctonia species on cotton and turf, Ustilago species on cereals and sugar cane, *Venturia inaequalis* (scab) on apples, Helminthosporium species on cereals, *Septoria nodorum* on wheat, *Botrytis cinerea* (gray mold) on strawberries, grapevines, ornamentals and vegetables, *Cercospora arachidicola* on peanuts, *Pseudocercosporella herpotrichoides* on wheat, barley, *Pyricularia oryzae* on rice, *Phytophthora infestans* on potatoes and tomatoes, Fusarium and Verticillium species on a variety of plants, *Plasmopara viticola* on grapevines and Alternaria species on vegetables and fruit.

The active compounds of the formula I can be present either in free form or in the form of their agriculturally utilizable or environmentally compatible salts. Such salts are, for example, acidic addition salts with inorganic or organic acids, for example hydrochloric acid, sulfuric acid, acetic acid, and other acids.

The active compounds of the formula I can also be employed in the protection of materials (protection of wood), for example against *Paecilomyces variotii*.

In general, the fungicidal compositions comprise from 0.1 to 95, preferably from 0.5 to 90, % by weight of active ingredient.

Depending on the nature of the desired effect, the rates of application are from 0.025 to 2, preferably 0.1 to 1, kg of active ingredient per ha.

In the treatment of seed, amounts of 0.001 to 50, preferably 0.01 to 10, g of active ingredient are generally required per kilogram of seed.

In the use form as fungicides, the agents according to the invention can also be present together with other active ingredients, e.g. with herbicides, insecticides, growth regulators, fungicides or else with fertilizers.

A mixture with other fungicides frequently results in a broader spectrum of fungicidal action. In particular when they are used in combination with other fungicidally active compounds, the active compounds of the formula I reduce the risk of resistance developing compared to when the active compounds are applied individually.

If the crop plants or the seeds are treated with combination preparations of active compounds of the formula I and other fungicidally active compounds, this application can be carried out simultaneously or successively. If the active compounds of the formula I are applied simultaneously with other fungicides, this is advantageously carried out by preparing an agrochemical mixture of the two active compounds, which mixture is then used for treating the crop plants or the seeds in a customary manner.

If the active compounds are used successively, this is advantageously carried out by applying the individual active compounds either within a short interval or within an interval of a plurality of days or weeks. By this combined application, it is possible to reduce the total frequency of the treatment of the plants or the seeds with fungicides.

For the purpose of the present invention, the term "combination preparations" includes, in principle, all agrochemical compositions comprising the active compounds of the formula I or II and one or more active compounds, in particular those having fungicidal activity, for example in the form of customary agrochemical mixtures. The term "combination preparations" furthermore also embraces those agrochemical preparations which comprise active compounds of the formula I and furthermore a reference that these active compounds are suitable for combined application with other active compounds in agriculture. Such a reference may be present, for example, in the form of a printed notice on the packaging of the commercial product or on the container holding the active compound of the formula I or the agrochemical composition comprising an active compound of the formula I. Alternatively, it is also possible for other agrochemical products to have corresponding references to the combined application with compounds of the formula I or II. In this context, such products are likewise combination preparations suitable for use in combination with active compounds of the formula I or II.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebis-dithiocarbamate), zinc (N,N'-propylenebisdithiocarbamate), N,N'-polypropylenebis (thiocarbamoyl)disulfide;

nitro derivatives, such as dinitro-(1-methylheptyl)phenyl crotonate, 2-sec-butyl-4,6-dinitrophenyl 3,3-dimethylacrylate, 2-sec-butyl-4,6-dinitrophenyl- isopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1,1,2,2-tetrachloroethylthio)-tetrahydrophthalimide, N-trichloromethylthiotetrahydrophthalimide, N-trichloromethylthiophthalimide, N-dichlorofluoromethylthio-N',N'-dimethyl-N-phenylsulfodiamide, 5-ethoxy-3-trichloromethyl-1,2,3-thiadiazole, 2-thiocyanatoethylthiobenzothiazole, 1,4-dichloro-2,5-dimethoxybenzene, 4-(2-chlorophenylhydrazono)-3-methyl-5-isoxazolone, pyridine-2-thione 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethyl-furan-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichlorethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, (2-chlorophenyl)-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thio-ureido)benzene, [2-(4-chlorophenyl)ethyl]-(1,1-dimethylethyl)-1H-1,2,4-triazole-1-ethanol, 1-[3-(2-chlorophenyl)-1-(4-fluoro-phenyl)oxiran-2-ylmethyl]-1H-1,2,4-triazole, and A variety of fungicides such as dodecylguanidine acetate, 3-[3-(3,5-dimethyl-2-oxycyclohexyl)-2-hydroxyethyl] glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-amino-butyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[(3,5-dichlorophenyl)-5-methyl-5-methoxymethyl-1,3-oxazolidine-2,4-dione, 3-(3,5-dichlorophenyl)-1-isopropyl-carbamoylhydantoin, N-(3,5-dichlorophenyl)-1,2-dimethylcyclo-propane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trif luoromethyl-3-chloro-2-aminopyridine, 1-((bis(4-fluorophenyl) methylsilyl)methyl)-1H-1,2,4-triazole, strobilurins such as methyl E-methoximino-[α-(o-tolyloxy)-o-tolyl]acetate, methyl E-2-{2-[6-(2-cyanophenoxy)pyridimin-4-yloxy]phenyl}-3-methoxyacrylate, methyl E-methoximino-[α-(2,5-dimethyloxy)-o-tolyl]acetamide, anilinopyrimidines such as N-(4,6-dimethylpyrimidin-2-yl)aniline, N-[4-methyl-6-(1-propynyl)pyrimidin-2-yl] aniline, N-(4-methyl-6-cyclopropylpyrimidin-2-yl) aniline, phenylpyrroles such as 4-(2,2-difluoro-1,3-benzodioxol-4-yl)-pyrrole-3-carbonitrile, cinnamamides such as 3-(4-chlorophenyl)-3-(3,4-dimethoxyphenyl)acryloylmorpholine.

The invention is illustrated in more detail using the working examples below:

EXAMPLE 1

1-Anilino-3-chloro-4-phenylpyrrol-2,5-dione
(Table 1, No. 1)

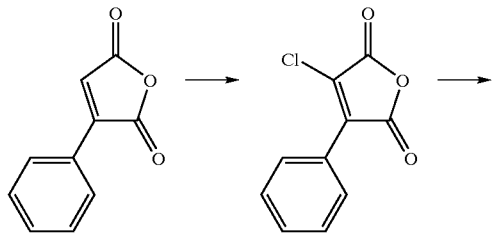

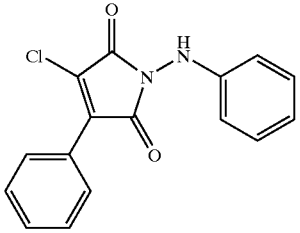

a) 3-Chloro-4-phenylfuran-2,5-dione

With ice-cooling, 10.0 g (57 mmol) of phenylmaleic anhydride were added to 57 ml of thionyl chloride, and the mixture was, over a period of 10 min, admixed dropwise with 9.08 g (115 mmol) of pyridine, the temperature being maintained at 10–12° C. The mixture was stirred at 10–12° C. for 30 min, heated at 75° C. for 10 min. using a preheated heating bath and allowed to cool, and excess thionylchloride was stripped off at 60° C. at reduced pressure. The residue was then boiled with 120 ml of toluene and filtered, and the residue was washed with 50 ml of hot toluene. The filtrate was concentrated under reduced pressure, titrated with petroleum ether and dried. Yield: 8.5 g, m.p. 82–83° C.

b) 1-Anilino-3-chloro-4-phenylpyrrol-2,5-dione 4.14 g (20 mmol) of 3-chloro-4-phenylfuran-2,5-dione were initially charged in 50 ml of chloroform and, at room temperature, admixed dropwise with stirring with 2.16 g (20 mmol) of phenyl hydrazine, and the mixture was stirred at room temperature overnight. The mixture was filtered, washed three times with sodium bicarbonate solution and once with water, dried over sodium sulfate and concentrated under reduced pressure. Yield: 5.4 g of a crystalline solid, m.p. 144–146° C.

EXAMPLE 2

1-Anilino-3-methylthio-4-phenylpyrrol-2,5-dione
(Table 1, No. 1041)

At room temperature, 22.3 g (75 mmol) of 1-anilino-3-chloro-4-phenylpyrrol-2,5-dione, dissolved in 220 ml of dimethylformamide, were admixed with stirring with 5.78 g (82 mmol) of sodium methylthiolate, and the mixture was stirred at room temperature overnight. The mixture was poured into water and extracted with methyl tert-butyl ether, and the extract was washed repeatedly with water, dried over sodium sulfate and concentrated under reduced pressure. For purification, the residue was titrated with cyclohexane. Yield: 19.4 g of a solid of m.p. 86–88° C.

EXAMPLE 3

3-Chloro-1-((4-fluorophenyl)amino)-4-phenylpyrrol-2,5-dione (Table 1, No. 27)

3.13 g (15 mmol) of 3-chloro-4-phenylfuran-2,5-dione and 2.44 g (15 mmol) of 4-fluorophenylhydrazine hydrochloride were initially charged in 50 ml of methylene chloride, and the mixture was, at room temperature, admixed dropwise with stirring with 1.52 g (15 mmol) of triethylamine and stirred at room temperature overnight. A further 50 ml of methylene chloride were added, and the mixture was washed three times with in each case 80 ml of water, dried over sodium sulfate and concentrated under reduced pressure. Yield: 3.9 g of a crystalline solid, m.p. 115–117° C.

EXAMPLE 4

3-Chloro-4-(4-chlorophenyl)-1-(N-methyl-N-phenylamino)-pyrrol-2,5-dione (Table 1, No. 23)

a) Potassium 3-(4-chlorophenyl)-3-cyanoacrylate 133 g (0.9 mol) of 50% strength aqueous glyoxylic acid was added dropwise with stirring to 91.2 g (0.6 mol) of (4-chlorophenyl)acetonitrile and 210 g (1.5 mol) of potassium carbonate in 1.2 l of methanol such that the reaction temperature increased to 35° C. The mixture was stirred at room temperature for 6 h and then filtered, and the residue was washed with methylene chloride and dried under reduced pressure. At room temperature, the crude product was stirred with 3 l of water for 1.5 h, and the residue was filtered off, washed with water and dried. Yield: 138 g of a solid of m.p. 241–242° C.

b) 3-(4-Chlorophenyl)furan-2,5-dione

With stirring, 80 ml of concentrated sulfuric acid were added dropwise to 138 g (0.57 mol) potassium 3-(4-chlorophenyl)-3-cyanoacrylate in 1.2 l of 88% strength formic acid. During the addition, the temperature increased to 50° C. The mixture was refluxed for 3 h and, after cooling, put into 10 l of ice-water and then stirred for 1 h, and the product was filtered off, washed with water and dried under reduced pressure. Yield: 86.0 g of m.p. 144–145° C.

c) 3-Chloro-4-(4-chlorophenyl)furan-2,5-dione

With ice-cooling, 15.0 g (72 mmol) of 3-(4-chlorophenyl)furan-2,5-dione were added to 72 ml of thionyl chloride, and the mixture was admixed dropwise over a period 10 min with 11.5 g (145 mmol) of pyridine, the temperature being maintained at 10–12° C. The mixture was stirred at 10–12° C. for 30 min, heated at 75° C. for 10 min using a preheated heating bath and allowed to cool, and excess thionyl chloride was removed at 60° C. under reduced pressure. The residue was boiled with 200 ml of toluene and filtered, and the residue was again boiled with 100 ml of toluene and filtered whilst still hot. The filtrate was concentrated under reduced pressure and the residue was boiled with 100 ml of petroleum ether, cooled, filtered off, washed once more with petroleum ether and dried under reduced pressure. Yield: 16.2 g, m.p. 110–112° C.

d) 3-Chloro-4-(4-chlorophenyl)-1-(N-methyl-N-phenylamino)pyrrol-2,5-dione 3.65 g (15 mmol) of 3-chloro-4-(4-chlorophenyl)furan-2,5-dione were initially charged in 75 ml of chloroform and, at room temperature, admixed dropwise with stirring with 1.83 g (15 mmol) of N-methyl-N-phenylhydrazine dissolved in 15 ml of chloroform, and the mixture was stirred at room temperature overnight. The mixture was then concentrated under reduced pressure and the residue was taken up in 200 ml of methylene chloride, washed three times with in each case 150 ml of water, dried over sodium sulfate and concentrated under reduced pressure. Yield: 4.6 g of a crystalline solid, m.p. 155–157° C.

EXAMPLE 5

1-Anilino-3-methylsulfinyl-4-phenylpyrrol-2,5-dione (Table 1, No. 1042) and 1-anilino-3-methylsulfonyl-4-phenylpyrrol-2,5-dione (Table 1, No. 1043)

At 40° C., 2.0 g (6.5 mmol) of 1-anilino-3-methylthio-4-phenylpyrrol-2,5-dione and 69 mg (0.2 mol) of sodium tungstate dihydrate in 20 ml of acetic acid were admixed dropwise with stirring with 1.5 g (13 mmol) of 30% strength hydrogen peroxide, and the mixture was kept at this temperature for 3 h. Another 0.3 g (2.6 mmol) of 30% strength hydrogen peroxide was then added, and the mixture was stirred at 40° C. for 4 h and then at room temperature overnight. The mixture was poured into 80 ml of water and the crude product was filtered off, washed with a little water and dried under reduced pressure. Silica gel chromatography using ethyl acetate/cyclohexane gave 0.45 g of 1-anilino-3-methylsulfinyl-4-phenylpyrrol-2,5-dione of m.p. 178–180° C. and 0.65 g of 1-anilino-3-methylsulfonyl-4-phenylpyrrol-2,5-dione of m.p. 194–196° C.

EXAMPLE 6

1-Anilino-3-bromo-4-phenylpyrrol-2,5-dione (Table 1, No. 486)

a) 3-Bromo-4-phenylfuran-2,5-dione

At 10° C., first 40.2 g (193 mmol) of thionyl bromide and then 15.3 g (193 mmol) of pyridine were added dropwise with stirring to 16.8 g (97 mmol) of phenylmaleic anhydride in 200 ml of toluene. The mixture was stirred at 10° C. for 30 min, heated at 75° C. for 30 min using a preheated heating bath and allowed to cool, and excess thionyl bromide was removed at 65° C. under reduced pressure. The mixture was then stirred with 150 ml of toluene and filtered, and the residue was washed twice with in each case 200 ml of toluene, and the filtrate was concentrated under reduced pressure. The crude product (9.3 g) still contained 25% of unreacted starting material and was used without further purification.

b) 1-Anilino-3-bromo-4-phenylpyrrol-2,5-dione 4.3 g (17 mmol) of 3-bromo-4-phenylfuran-2,5-dione were initially charged in 40 ml of chloroform and, at room temperature, admixed dropwise with stirring with 1.84 g (17 mmol) of phenylhydrazine in 15 ml of chloroform, and the mixture was stirred at room temperature overnight. The mixture was filtered, the filtrate was concentrated under reduced pressure and the residue was purified by silica gel chromatography using ethyl acetate/cyclohexane. Yield: 1.9 g, m.p. 146–147° C.

EXAMPLE 7

Activity Against *Phytophthora infestans* on Tomatoes

Leaves of potted plants cv. "Große Fleischtomate" were sprayed to run off point with an aqueous suspension made up of a stock solution of 10% of active compound, 63% of cyclohexanone and 27% of emulsifier. The next day, the leaves were infected with an aqueous zoospore suspension of *Phytophthora infestans*. The plants were then kept in a chamber saturated with water vapor at 16–18° C. After 6 days, the tomato blight on the untreated but infected control plants had developed to such an extent that the infection could be determined visually in percent.

| Active compound | % infection of the leaves after application of 250 ppm-containing aqueous preparation of active compound |
|---|---|
| Compound (I) | 90 |
| Untreated | |

It is evident from the tests that, compared to the untreated plants, the treated plants show considerably less damage caused by harmful fungi. Accordingly, the active compounds according to the invention have good fungicidal activity. In particular, they have a protective effect against harmful fungi.

EXAMPLE 8

Activity Against *Plasmopara viticola*

Leaves of potted vines cv. "Müller-Thurgau" were sprayed to run off point with an aqueous preparation of active compound prepared from a stock solution of 10% of active compound, 63% of cyclohexanone and 27% of emulsifier. To be able to assess the long-term activity of the substances, the plants were kept in a greenhouse for 7 days after the spray coating had dried on. Only then were the leaves inoculated with an aqueous zoospore suspension of *Plasmopara viticola*. The plants were then first kept in a chamber saturated with water vapor at 24° C. for 48 hours, and subsequently in a greenhouse at 20–30° C. for 5 days. After this time, the plants were once more placed in a humid chamber for 16 hours to promote the eruption of sporangiophores. The extent of the development of the infection on the underside of the leaves was then determined visually.

| Active compound | % infection of the leaves after application of 250 ppm-containing aqueous preparation of active compound |
|---|---|
| Compound (I) | 85 |
| Untreated | |

We claim:

1. An agrochemical composition having fungicidal action, comprising compounds of the formula I

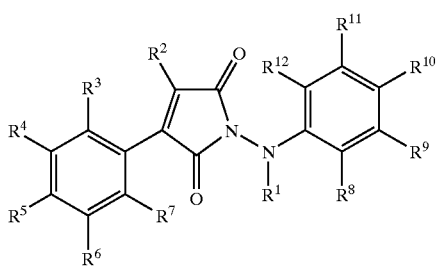

where:
$R^1$ is hydrogen, $C_1$–$C_6$-alkyl, $C_1$–$C_6$-alkylcarbonyl, formyl or $C_1$–$C_6$-haloalkylcarbonyl;
$R^2$ is halogen, $C_1$–$C_6$-alkylthio, $C_1$–$C_6$-alkoxy, $C_3$–$C_6$-cycloalkyl-$C_1$–$C_6$-alkoxy, $C_1$–$C_6$-alkoxy-$C_1$–$C_6$-alkyl, halo-$C_1$–$C_6$-alkoxy, $C_1$–$C_6$-alkylsulfonyl, $C_1$–$C_6$-alkylsulfinyl, halo-$C_1$–$C_6$-alkylsul-fonyl, cyano or a radical $NR^{13}R^{14}$;
$R^3$–$R^{12}$ are hydrogen, halogen, $C_1$–$C_8$-cycloalkyl, $C_1$–$C_6$-alkyl, halo-$C_1$–$C_6$-alkyl, $C_1$–$C_6$-alkoxy, halo-$C_1$–$C_6$-alkoxy, $C_1$–$C_6$-alkyl-sulfonyl, halo-$C_1$–$C_6$-alkylsulfonyl, formyl, $C_1$–$C_6$-alkylcarbonyl, cyano, $C_1$–$C_6$-alkylthio or phenyl, which may be unsubstituted or substituted by halogen, $C_1$–$C_6$-alkyl or halo-$C_1$–$C_6$-alkyl,
$R^{13}$ is hydrogen, $C_1$–$C_6$-alkyl,
$R^{14}$ is $C_1$–$C_6$-alkyl, $C_1$–$C_8$-cycloalkyl or, together with $R^{13}$ and the nitrogen atom to which they are attached, a saturated or unsaturated heterocyclic five- or six-membered ring which contains one or two heteroatoms selected from the group consisting of nitrogen and oxygen,
or agriculturally useful salts thereof.

2. A composition as claimed in claim 1, wherein $R^1$ is hydrogen, $C_1$–$C_6$-alkyl, $C_1$–$C_6$-alkylcarbonyl or formyl.

3. A composition as claimed in claim 2, wherein $R^1$ is hydrogen, methyl, formyllor acetyl.

4. A composition as claimed in claim 1, wherein $R^2$ is halogen, $C_1$–$C_6$-alkylthio, $C_1$–$C_6$-alkylsulfonyl, $C_1$–$C_6$-alkylsulfinyl or halo-$C_1$–$C_6$-alkoxy.

5. A composition as claimed in claim 4, wherein $R^2$ is chlorine, bromine, methylthio, methylsulfonyl, methylsulfinyl or difluoromethoxy.

6. A composition as claimed in claim 1, wherein one or more of the radicals $R^3$–$R^{12}$ have the following meanings: fluorine, chlorine, methyl, ethyl, propyl, butyl, trifluoromethyl, difluoromethyl, trifluoromethoxy, difluoromethoxy, methoxy, methylthio, cyano, and at least three of the radicals $R^3$–$R^{12}$ are hydrogen.

7. A composition as claimed in claim 6, wherein four to nine of the radicals $R^3$–$R^{12}$ are hydrogen.

8. A composition as claimed in claim 1, wherein two to five of the radicals $R^8$–$R^{12}$ are hydrogen.

9. A composition as claimed in claim 8, wherein three or four of the radicals $R^8$–$R^{12}$ are hydrogen.

10. A composition as claimed in claim 1, wherein two to five of the radicals $R^3$–$R^7$ are hydrogen.

11. A composition as claimed in claim 10, wherein three or four of the radicals $R^3$–$R^7$ are hydrogen.

12. A composition as claimed in claim 1, wherein at least two of the radicals $R^8$–$R^{12}$ and at least two of the radicals $R^3$–$R^7$ are hydrogen.

13. A composition as claimed in claim 1, wherein one, two or three of the radicals $R^3$–$R^{12}$ are halogen, $C_1$–$C_6$-alkyl, $C_1$–$C_6$-haloalkyl, $C_1$–$C_6$-alkoxy or $C_1$–$C_6$-haloalkoxy and the other radicals $R^3$–$R^{12}$ are hydrogen.

14. A composition as claimed in claim 13, wherein the radicals $R^3$–$R^{12}$ are selected from the group consisting of fluorine, chlorine, bromine, iodine, methyl, ethyl, propyl, butyl, trifluoromethyl, trifluoromethoxy and difluoromethoxy.

15. A composition as claimed in claim 1, comprising a compound of formula (I) which is selected from the group consisting of:

1-anilino-3-chloro-4-phenylpyrrol-2,5-dione, 1-anilino-3-methylthio-4-phenylpyrrol-2,5-dione, 3-chloro-4-(4-chlorophenyl)-1-(N-methyl-N-phenylamino)-pyrrol-2,5-dione, 1-anilino-3-methylsulfinyl-4-phenylpyrrol-2,5-dione, 1-anilino-3-methylsulfonyl-4-phenylpyrrol-2,5-dione, and 1-anilino-3-bromo-4-phenylpyrrol-2,5-dione.

16. A method for controlling harmful fungi, wherein the harmful fungi, their habitat or the plants, areas, materials or spaces to be kept free from them are treated with a fungicidally effective amount of the composition defined in claim 1.

* * * * *

UNITED STATES PATENT AND TRADEMARK OFFICE
CERTIFICATE OF CORRECTION

PATENT NO.     : 6,586,369 B1
DATED          : July 1, 2003
INVENTOR(S)    : Rheinheimer et al.

It is certified that error appears in the above-identified patent and that said Letters Patent is hereby corrected as shown below:

<u>Column 45,</u>
Lines 51 and 55, "alkylsul-fonyl" should be -- alkylsulfonyl --.

<u>Column 46,</u>
Line 8, "formyllor" should be -- formyl or --.

Signed and Sealed this

Twenty-third Day of September, 2003

JAMES E. ROGAN
*Director of the United States Patent and Trademark Office*